United States Patent [19]

Laborde et al.

[11] Patent Number: 5,342,844
[45] Date of Patent: Aug. 30, 1994

[54] 7-SUBSTITUTED QUINOLONES AND NAPHTHYRIDONES AS ANTIBACTERIAL AGENTS

[75] Inventors: Edgardo Laborde, Canton; Mel Schroeder, Dexter, both of Mich.

[73] Assignee: Warner-Lambert Company, Morris Plains, N.J.

[21] Appl. No.: 14,286

[22] Filed: Feb. 5, 1993

Related U.S. Application Data

[62] Division of Ser. No. 832,188, Feb. 6, 1992, Pat. No. 5,221,676.

[51] Int. Cl.$^5$ ............... A61K 31/44; C07D 227/08; C07D 471/04
[52] U.S. Cl. .................................. 514/300; 514/312; 514/314; 546/123; 546/156; 546/256; 546/281
[58] Field of Search ................ 514/300, 312, 314; 546/123, 156, 256, 281

[56] References Cited

U.S. PATENT DOCUMENTS

| | | | |
|---|---|---|---|
| 4,801,584 | 1/1989 | Yokose et al. | 514/183 |
| 4,886,810 | 12/1989 | Matsumoto et al. | 546/156 |
| 4,886,810 | 12/1989 | Matsumoto et al. | 514/312 |

FOREIGN PATENT DOCUMENTS 0167763  1/1986  European Pat. Off. .

*Primary Examiner*—Mukund J. Shah
*Assistant Examiner*—Y. N. Gupta
*Attorney, Agent, or Firm*—Ronald A. Daignault; Charles W. Ashbrook

[57] ABSTRACT

7-Substituted quinolones and naphthyridones are described as antibacterial agents as well as a process for their manufacture, compositions therefor, wherein the 7-substituent is a pyrrolidine ring substituted at the 3-position by a substituted aromatic hydrocarbon or a heteroaromatic group.

19 Claims, No Drawings

7-SUBSTITUTED QUINOLONES AND NAPHTHYRIDONES AS ANTIBACTERIAL AGENTS

This is a divisional of U.S. application Ser. No. 832,188 filed Feb. 6, 1992, now U.S. Pat. No. 5,221,767.

BACKGROUND OF THE INVENTION

The present invention is related to novel 7-substituted quinolones and naphthyridones which are useful in treating bacterial infections, particularly against gram-positive and gram-negative bacteria. The 7-substituent is a pyrrolidine ring substituted at the 3-position by a substituted aromatic hydrocarbon or a heteroaromatic group.

SUMMARY OF THE INVENTION

Accordingly, the present invention includes 7-substituted quinolones and naphthyridones of Formula I:

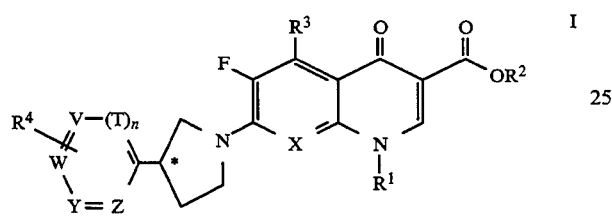

wherein
* denotes an asymmetric carbon;
X is C—H, C—F, C—Cl, C—OCH$_3$, C—CF$_3$, or N;
R$^1$ is a C$_1$-C$_4$-alkyl, C$_3$-C$_6$-cycloalkyl, or phenyl substituted by one or more halogen atoms;
R$^2$ is hydrogen, alkyl of 1 to 4 carbon atoms, or a cation;
R$^3$ is hydrogen, amino, or methyl;
V, W, Y, and Z are each independently C—H, oxygen, nitrogen, or sulfur;
T is C—H or nitrogen;
n is 0 or 1;
R$^4$ is hydrogen or one, two or three substituents independently selected from C$_1$-C$_4$-alkyl, halo-substituted C$_1$-C$_4$-alkyl, hydroxy-substituted C$_1$-C$_4$-alkyl, halogen, hydroxy, C$_1$-C$_4$-alkoxy, mercapto, amino, mono-(C$_1$-C$_4$-alkyl)amino, di-(C$_1$-C$_4$-alkyl)amino, formamido, mono-(C$_1$-C$_4$-alkyl)amido, di-(C$_1$-C$_4$-alkyl)amido, cyano, nitro, C$_1$-C$_4$-alkoxycarbonyl, carboxyl, aminomethyl, mono-(C$_1$-C$_4$-alkyl)aminomethyl, di-(C$_1$-C$_4$-alkyl)aminomethyl, wherein free hydroxy and amino groups may be protected;
with the proviso that when T, V, W, Y, and Z are C—H and n is 1, R$^4$ is aminomethyl, mono-(C$_1$-C$_4$-alkyl)aminomethyl or di-(C$_1$-C$_4$-alkyl)aminomethyl, and their pharmaceutically acceptable acid addition or quaternary ammonium salts thereof, when taken together, V, W, Y, Z, T, and R$^4$ contain at least one amino or oxygen function capable of acting as a proton acceptor.

The invention also includes a pharmaceutical composition comprising an antibacterially effective amount of a compound according to Formula I or a pharmaceutically acceptable salt thereof, in combination with a pharmaceutically acceptable carrier or diluent.

The invention further includes a method for treating bacterial infections in mammals, which comprises administering an antibacterially effective amount of the above defined pharmaceutical composition to a mammal in need thereof.

In another aspect, the invention includes a process for the preparation of a compound of Formula I, which comprises reacting a compound of Formula II:

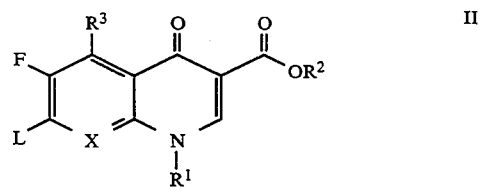

where L is fluorine, chlorine, or other leaving group, and X, R$^1$, R$^2$, and R$^3$ are as defined previously, with a pyrrolidine of Formula III:

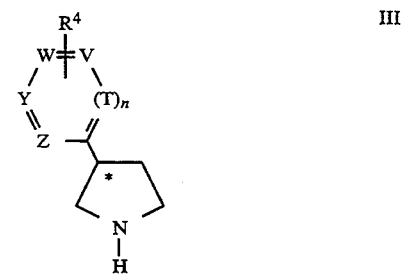

wherein * denotes an asymmetric carbon and T, V, W, Y, Z, R$^4$, and n are as defined previously.

The invention in still another aspect includes a process for the synthesis of pyrrolidines of Formula IV:

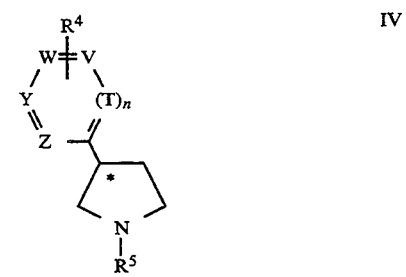

wherein* denotes an asymmetric carbon and T, V, W, Y, Z, R$^4$, and n are as defined previously;
R$^5$ is hydrogen or an amino protecting group such as benzyl, (R)- or (S)-1-methylbenzyl, benzyloxycarbonyl, or tert-butoxycarbonyl; comprising:

(a) preparation, by known methods, of a substituted ethylene derivative of the Formula V;

(b) reaction of the above ethylene derivative with an azomethine ylide of Formula VI:

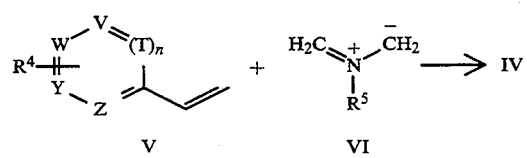

Certain novel intermediates in the process for preparing compounds of Formula I are also included in the present invention. They include pyrrolidines of Formula IV as defined above, excluding 2- and 3-pyridyl groups on pyrrolidine.

DETAILED DESCRIPTION AND PREFERRED EMBODIMENTS

Substituents for the compounds of Formula I are hereafter defined:

The $C_1$–$C_4$-alkyl or alkoxy groups comprise both straight and branched carbon chains of one to four carbon atoms and include methyl, propyl, 1-methylethyl, n-butyl, 1-methylpropyl, 2-methylpropyl, and 1,1-dimethylethyl.

The cycloalkyl groups contemplated by the invention comprise those having three to six carbon atoms such as cyclopropyl, cyclobutyl, cyclopentyl, and cyclohexyl.

The hydroxyalkyl groups contemplated by the invention comprise those having two to four carbon atoms such as 2-hydroxyethyl, 2- or 3-hydroxypropyl, 2-, 3-, or 4-hydroxybutyl.

The term haloalkyl is intended to include halogen substituted straight and branched carbon chains of from two to four carbon atoms. Those skilled in the art will recognize that the halogen substituents may not be present on the α-carbon atom of the chain. Representative of such groups are β-fluoroethyl, β-chloroethyl, β,β-dichloroethyl, β-chloropropyl, β-chloro-2-propyl, and the like.

The term halogen is intended to include fluorine, chlorine, bromine, and iodine.

T, W, Y, Z, and $R^4$ together define the substituent on the 3-position of the pyrrolidine ring located at the 7-position of the quinolones and naphthyridones of Formula I. The groups contemplated at the 3-position of the pyrrolidine ring are substituted aromatic or heteroaromatic groups. Substituted aromatic groups are phenyl substituted by $R^4$ wherein $R^4$ is limited to aminomethyl, mono-($C_1$–$C_4$-alkyl)aminomethyl or di-($C_1$–$C_4$-alkyl)aminomethyl.

The heteroaromatic groups contemplated by the definition of T, W, Y, Z, n, and substituent $R^4$ are 5- or 6-membered unsaturated rings having one to four heteroatoms selected from nitrogen, oxygen, and sulfur. They include, for example: 2- and 3-pyrrolyl, 2- and 3-furanyl, 2- and 3-thiophenyl, 3-, 4-, and 5-pyrazolyl, 3-, 4-, and 5-isoxazolyl, 3-, 4-, and 5-isothiazolyl, 2-, 4-, and 5-imidazolyl, 2-, 4-, and 5-oxazolyl, 2-, 4-, and 5-thiazolyl, 1,3,4-triazol-2-yl, 1,3,4-oxadiazol-2-yl, 1,3,4-thiadiazol-2-yl, 1,2,4-triazol-3(or 5)-yl, 1,2,4-oxadiazol-3(or 5)-yl, 1,2,4-thiadiazol-3(or 5)-yl, 5-tetrazolyl, 3- and 4-pyridazinyl, 2-, 4-, and 5-pyrimidinyl, 2-pyrazinyl, and 2-, 3-, and 4-pyridinyl. The heteroaromatic groups may also be substituted by substituents defined by $R^4$ without the limitations as in the aromatic group.

Free hydroxyl and amino groups may be protected by known protective groups which are easily removable by hydrolysis or hydrogenolysis.

Groups which protect hydroxy are, for example, benzyl, p-methoxybenzyl, acetyl, tetrahydropyranyl, tert-butyl, 2-chloroethyl, methoxy, methyl, trimethylsilyl, etc.

The groups are attached by reacting the free hydroxy group or its anion with the appropriate halide (or other electrophile) under conditions known in the art.

The protective group may then be easily removed by hydrogenation, or acid- or base-catalyzed hydrolysis.

Groups protecting amino are, for example, benzyl, p-methoxybenzyl, benzyloxycarbonyl, tert-butyloxycarbonyl, acetyl, trifluoroacetyl, trimethylsilyl, etc.

The groups are attached by reacting the free amine with the appropriate halide, acid chloride or anhydride, carbonate, or chlorocarbonate under conditions known in the art.

The amino protecting group may be easily removed by hydrogenation, or mild acid or base-catalyzed hydrolysis.

Certain compounds of the invention may exist in optically active forms. The pure R isomer, pure S isomer as well as mixtures thereof, including the racemic mixtures, are contemplated by the invention. Additional asymmetric carbon atoms may be present in a substituent such as an alkyl group. All such isomers as well as mixtures thereof are intended to be included in the invention. Certain side chains may contain more than one chiral center. In these cases the diastereoisomers may be separated and utilized individually. All such mixtures and separated mixtures are contemplated by the invention.

The compounds of the invention are capable of forming both pharmaceutically acceptable acid addition and/or base salts, wherein $R^2$ is a cation. Base salts are formed with metals or amines, such as alkali and alkaline earth metals or organic amines. Examples of metals used as cations are sodium, potassium, magnesium, calcium, and the like. Also included are heavy metal salts such as, for example, silver, zinc, cobalt, and cerium. Such heavy metal salts are effective in the treatment of burns, especially when applied to the affected surface of a burn victim either directly or in combination with a physiologically acceptable carrier such as a water dispersible, hydrophilic carrier. Examples of suitable amines are N,N'-dibenzylethylenediamine, chloroprocaine, choline, diethanolamine, ethylenediamine, N-methylglucamine, and procaine.

Pharmaceutically acceptable acid addition salts are formed with organic and inorganic acids.

Examples of suitable acids for salt formation are hydrochloric, sulfuric, phosphoric, acetic, lactic, citric, oxalic, malonic, salicylic, malic, gluconic, fumaric, succinic, ascorbic, maleic, methanesulfonic, and the like. The salts are prepared by contacting the free base form with a sufficient amount of the desired acid to produce either a mono or di salt in the conventional manner. The free base form may be regenerated by treating the salt form with a base. For example, dilute solutions of aqueous base may be utilized. Dilute aqueous sodium hydroxide, potassium carbonate, ammonia, and sodium bicarbonate solutions are suitable for this purpose. The free base forms differ from their respective salt forms somewhat in certain physical properties such as solubility in polar solvents, but the salts are otherwise equivalent to their respective free base forms for purposes of the invention. Use of excess base where $R^1$ is hydrogen gives the corresponding basic salt.

Certain compounds of the invention are also capable of forming quaternary ammonium salts. These salts are formed by reaction of an available nitrogen, e.g., on a heteroaromatic ring, with a $C_1$–$C_4$-alkyl or aralkyl halide, preferably an iodide. Preferred alkyl and aralkyl groups are methyl and benzyl.

The compounds of the invention can exist in unsolvated as well as solvated forms, including hydrated forms. In general, the solvated forms, including hydrated forms and the like are equivalent to the unsolvated forms for purposes of the invention.

Preferred compounds of the present invention and of Formula I are those wherein X, $R^2$, $R^3$, T, V, W, Y, Z, and n are as defined above; $R^1$ is $C_3$-$C_6$-cycloalkyl or phenyl substituted by one or more halogen atoms, and $R^4$ is hydrogen, hydroxy, $C_1$-$C_4$-alkoxy, hydroxy substituted $C_1$-$C_4$-alkyl, amino, mono-($C_1$-$C_4$-alkyl)amino, di-($C_1$-$C_4$alkyl)amino, aminomethyl, mono-($C_1$-$C_4$-alkyl)aminomethyl or di-($C_1$-$C_4$-aminomethyl.

More preferred compounds of Formula I are those wherein $R^2$, T, V, W, Y, Z, and n are as defined above; X is C—H, C—F, C—Cl, C—OCH$_3$, or N; $R^1$ is cyclopropyl or 2,4-difluorophenyl; $R^3$ is hydrogen or amino, and $R^4$ is hydrogen, hydroxy, hydroxymethyl, amino, methylamino, dimethylamino, aminomethyl, methylaminomethyl, or dimethylaminomethyl.

As further preferred embodiments for compounds of Formula I, when n is 1, V, W, Y, and Z are each C—H, T is C—H or N or at least one of V, W, Y, or Z is N; when n is 0, V is C—H, N, O, or S; Y is C—H, N or S, and W and Z are each independently C—H or N.

Still more preferred compounds of this invention and of Formula I are those wherein $R^2$ is hydrogen or a cation; T, V, W, Y, Z, and n when taken together form an aromatic or heteroaromatic ring selected from the group consisting of 2- and 3-pyrrolyl, 2- and 3-furanyl, 2- and 3-thiophenyl, 3-, 4- and 5-pyrazolyl, 2-, 4-, and 5-thiazolyl, 1,3,4-oxadiazol-2-yl, 1,2,4-oxadiazol-3(or 5)-yl, 1,2,4-thiadiazol-3(or 5)-yl, 1,3,4-thiadiazol-2-yl, 2-, 4-, and 5-pyrimidinyl, 2-pyrazinyl, 2-, 3-, 4-pyridinyl, and phenyl; X is C—H, C—F, C—Cl, C—OCH$_3$, or N; $R^1$ is cyclopropyl or 2,4-difluorophenyl; $R^3$ is hydrogen or amino, and $R^4$ is hydrogen, hydroxy, hydroxymethyl, amino, methylamino, dimethylamino, aminomethyl, methylaminomethyl, or dimethylaminomethyl, with the same proviso that when T, V, W, Y, Z, and n are taken together to form a phenyl ring, $R^4$ is aminomethyl, methylaminomethyl, or dimethylaminomethyl.

Most preferred compounds of Formula I are those wherein $R^2$ is hydrogen or a cation; T, V, W, Y, Z, and n when taken together form an aromatic or heteroaromatic ring selected from 2- and 3-pyrrolyl, 2- and 3-furanyl-, 2- and 3-thiophenyl, 3-, 4-, and 5-pyrazolyl, 1,2,4-oxadiazol-3(or 5)-yl, 2-, 3-, and 4-pyridinyl, and phenyl; X is C—H, C—F, C—Cl, C—OCH$_3$, or N; $R^1$ is cyclopropyl or 2,4-difluorophenyl; $R^3$ is hydrogen or amino, and $R^4$ is hydrogen, hydroxy, hydroxymethyl, amino, or aminomethyl, with the same proviso that when T, V, W, Y, Z, and n are taken together to form a phenyl ring, $R^4$ is aminomethyl.

Particularly valuable compounds of Formula I are

7-[3-[2-(aminomethyl)phenyl]-1-pyrrolidinyl]-1-cyclopropyl-6-fluoro-1,4-dihydro-4-oxo-1,8-naphthyridine-3-carboxylic acid;

7-[3-[2-(aminomethyl)phenyl]-1-pyrrolidinyl]-1-cyclopropyl-6-fluoro-1,4-dihydro-4-oxo-3-quinolinecarboxylic acid;

5-amino-7-[3-[2-(aminomethyl)phenyl]-1-pyrrolidinyl]-1-cyclopropyl-6,8-difluoro-1,4-dihydro-4-oxo-3-quinolinecarboxylic acid;

7-[3-[2-(aminomethyl)phenyl]-1-pyrrolidinyl]-1-cyclopropyl-6-fluoro-1,4-dihydro-8-methoxy-4-oxo-3quinolinecarboxylic acid;

7-[3-[3-(aminomethyl)phenyl]-1-pyrrolidinyl]-1-cyclopropyl-6-fluoro-1,4-dihydro-4-oxo-1,8-naphthyridine-3-carboxylic acid;

7-[3-[3-(aminomethyl)phenyl]-1-pyrrolidinyl]-1-cyclopropyl-6-fluoro-1,4-dihydro-4-oxo-3-quinolinecarboxylic acid;

5-amino-7-[3-[3-(aminomethyl)phenyl]-1-pyrrolidinyl]-1-cyclopropyl-6,8-difluoro-1,4-dihydro4-oxo-3-quinolinecarboxylic acid;

7-[3-[4-(aminomethyl)phenyl]-1-pyrrolidinyl]-1-cyclopropyl-6-fluoro-1,4-dihydro-4-oxo-1,8-naphthyridine-3-carboxylic acid;

7-[3-[4-(aminomethyl)phenyl]-1-pyrrolidinyl]-1-cyclopropyl-6-fluoro-1,4-dihydro-4-oxo-3-quinolinecarboxylic acid;

5-amino-7-[3-[4-(aminomethyl)phenyl]-1-pyrrolidinyl]-1-cyclopropyl-6,8-difluoro-1,4-dihydro-4-oxo-3-quinolinecarboxylic acid;

1-cyclopropyl-6-fluoro-1,4-dihydro-7-[3-[3-[(methylamino)methyl]phenyl]-1-pyrrolidinyl]-4-oxo-3quinolinecarboxylic acid;

5-amino-1-cyclopropyl-6,8-difluoro-1,4-dihydro-7-[3-[3-[(methylamino)methyl]phenyl]-1-pyrrolidinyl]-4-oxo-3-quinolinecarboxylic acid;

1-cyclopropyl-6-fluoro-1,4-dihydro-7-[3-[4-[(methylamino)methyl]phenyl]-1-pyrrolidinyl]-4-oxo-3quinolinecarboxylic acid;

5-amino-1-cyclopropyl-6,8-difluoro-1,4-dihydro-7-[3-[4-[(methylamino)methyl]phenyl]-1-pyrrolidinyl]-4-oxo-3-quinolinecarboxylic acid;

1-cyclopropyl-6-fluoro-1,4-dihydro-4-oxo-7-[3-(2-pyridinyl)-1-pyrrolidinyl]-1,8-naphthyridine-3-carboxylic acid;

1-cyclopropyl-6-fluoro-1,4-dihydro-4-oxo-7-[3-(2-pyridinyl)-1-pyrrolidinyl]-3-quinolinecarboxylic acid;

5-amino-1-cyclopropyl-6,8-difluoro-1,4-dihydro-4-oxo-7-[3-(2-pyridinyl)-1-pyrrolidinyl]-3-quinolinecarboxylic acid;

1-cyclopropyl-6-fluoro-1,4-dihydro-4-oxo-7-[3-(3-pyridinyl)-1-pyrrolidinyl]-1,8-naphthyridine-3-carboxylic acid;

1-cyclopropyl-6-fluoro-1,4-dihydro-4-oxo-7-[3-(3-pyridinyl)-1-pyrrolidinyl]-3-quinolinecarboxylic acid;

5-amino-1-cyclopropyl-6,8-difluoro-1,4-dihydro-4-oxo-7-[3-(3-pyridinyl)-1-pyrrolidinyl]-3-quinolinecarboxylic acid;

1-cyclopropyl-6-fluoro-1,4-dihydro-4-oxo-7-[3-(4-pyridinyl)-1-pyrrolidinyl]-1,8-naphthyridine-3-carboxylic acid;

1-cyclopropyl-6-fluoro-1,4-dihydro-4-oxo-7-[3-(4-pyridinyl)-1-pyrrolidinyl]-3-quinolinecarboxylic acid;

5-amino-1-cyclopropyl-6,8-difluoro-1,4-dihydro-4-oxo-7-[3-(4-pyridinyl)-1-pyrrolidinyl]-3-quinolinecarboxylic acid;

7-[3-(3-amino-2-pyridinyl)-1-pyrrolidinyl]-1-cyclopropyl-6-fluoro-1,4-dihydro-4-oxo-3-quinolinecarboxylic acid;

7-[3-[3-(aminomethyl)-2-pyridinyl]-1-pyrrolidinyl]-1-cyclopropyl-6-fluoro-1,4-dihydro-4-oxo-3-quinolinecarboxylic acid;

5-amino-7-[3-[3-(aminomethyl)-2-pyridinyl]-1-pyrrolidinyl]-1-cyclopropyl-6,8-difluoro-1,4-dihydro-4-oxo-3-quinolinecarboxylic acid;

1-(2,4-difluorophenyl)-6-fluoro-1,4-dihydro-4-oxo-7-[3-(3-pyridinyl)-1-pyrrolidinyl]-1,8-naphthyridine-3-carboxylic acid;

7-[3-[3-(aminomethyl)phenyl]-1-pyrrolidinyl]-1-(2,4-difluorophenyl)-6-fluoro-1,4-dihydro-5-methyl-4-oxo-3-quinolinecarboxylic acid;

7-[3-[2-(aminomethyl)-1H-imidazol-4-yl]-1-pyrrolidinyl]-1-cyclopropyl-6-fluoro-1,4-dihydro-8-methoxy-5-methyl-4-oxo-3-quinolinecarboxylic acid;

7-[3-[2-(aminomethyl)-4-thiazolyl]-1-pyrrolidinyl]-1-cyclopropyl-6-fluoro-1,4-dihydro-4-oxo-1,8-naphthyridine-3-carboxylic acid;

7-[3-(5-amino-4-thiazolyl)-1-pyrrolidinyl]-1-cyclopropyl-6-fluoro-1,4-dihydro-5-methyl-4-oxo-3-quinolinecarboxylic acid;

5-amino-1-cyclopropyl-6,8-difluoro-1,4-dihydro-7-[3-[4-(hydroxymethyl)-2-thiazolyl]-1-pyrrolidinyl]-4-oxo-3-quinolinecarboxylic acid;

5-amino-1-cyclopropyl-6,8-difluoro-1,4-dihydro-7-[3-(1H-imidazol-2-yl)-1-pyrrolidinyl]-4-oxo-3-quinolinecarboxylic acid;

7-[3-(3-amino-1,2,4-oxadiazol-5-yl)-1-pyrrolidinyl]-1-cyclopropyl-6-fluoro-1,4-dihydro-4-oxo-1,8-naphthyridine-3-carboxylic acid;

5-amino-7-[3-(4-amino-2-thiazolyl)-1-pyrrolidinyl]-1-cyclopropyl-6,8-difluoro-1,4-dihydro-4-oxo-3-quinolinecarboxylic acid;

5-amino-7-[3-[3-(aminomethyl)-1,2,4-oxadiazol-5-yl]-1-pyrrolidinyl]-1-cyclopropyl-6,8-difluoro-1,4-dihydro-4-oxo-3-quinolinecarboxylic acid;

5-amino-7-[3-[3-(aminomethyl)-1H-1,2,4-triazol-5-yl]-1-pyrrolidinyl]-1-cyclopropyl-6,8-difluoro-1,4-dihydro-4-oxo-3-quinolinecarboxylic acid;

7-[3-(5-amino-1,3,4-oxadiazol-2-yl)-1-pyrrolidinyl]-1-cyclopropyl-6-fluoro-1,4-dihydro-4-oxo-1,8-naphthyridine-3-carboxylic acid;

7-[3-(3-amino-1H-1,2,4-triazol-5-yl)-1-pyrrolidinyl]-1-cyclopropyl-6-fluoro-1,4-dihydro-4-oxo-3-quinolinecarboxylic acid;

1-cyclopropyl-6-fluoro-1,4-dihydro-4-oxo-7-[3-(2-pyrimidinyl)-1-pyrrolidinyl]-1,8-naphthyridine-3-carboxylic acid;

1-cyclopropyl-6,8-difluoro-1,4-dihydro-4-oxo-7-[3-(4-pyrimidinyl)-1-pyrrolidinyl]-3-quinolinecarboxylic acid, and 5-amino-1-cyclopropyl-6-fluoro-1,4-dihydro-8-methoxy-4-oxo-7-[3-(2-pyrazinyl)-1-pyrrolidinyl]-3-quinolinecarboxylic acid.

The compounds of the present invention and of Formula I, as well as intermediates of Formula III, may be prepared generally as described above.

Particularly, the compounds of Formula I may be prepared, for example, as illustrated by the following reaction schemes.

SCHEME I

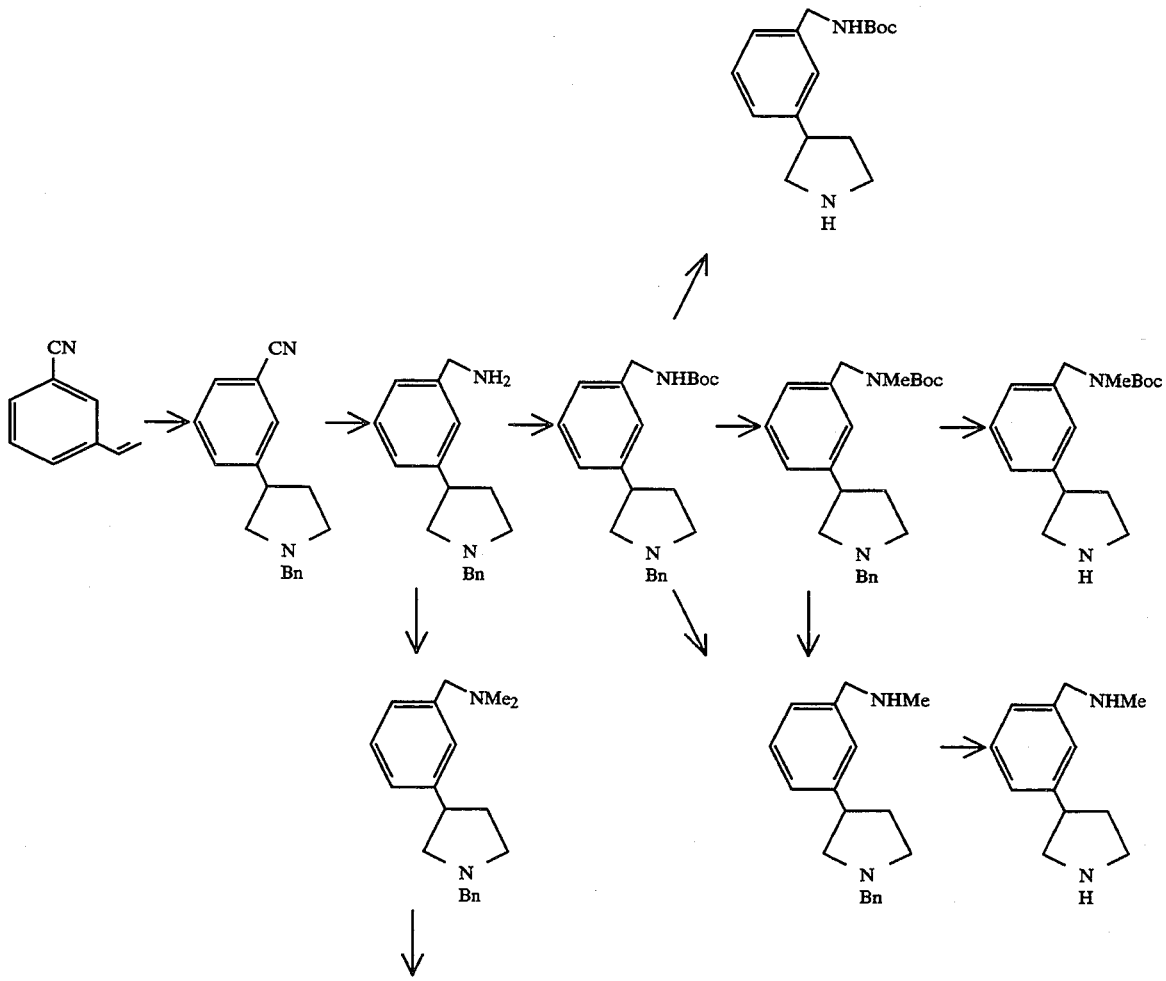

-continued
SCHEME I

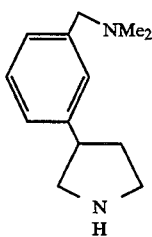

SCHEME II

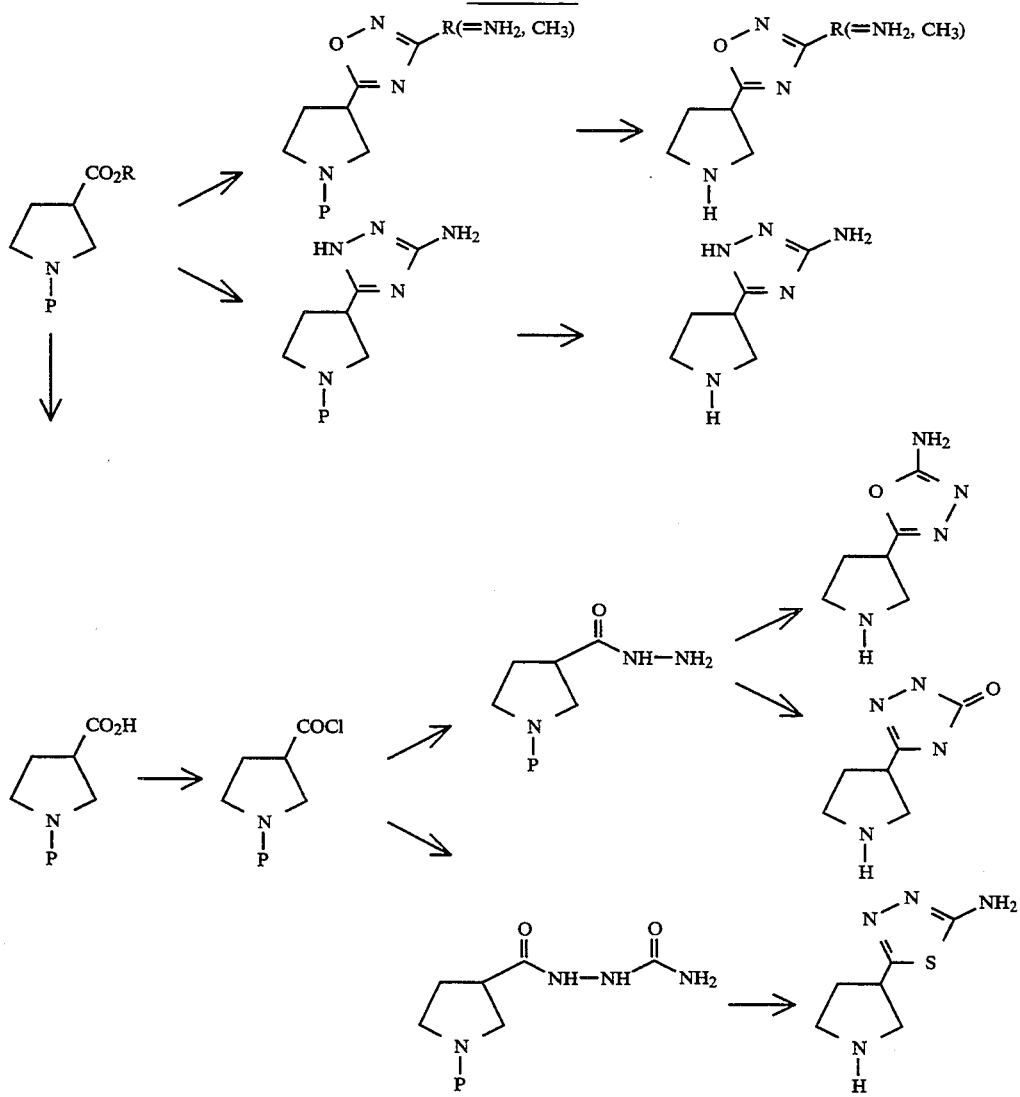

Starting from a vinylbenzene derivative or any vinyl-heteroaromatic derivative (Scheme I), which is commercially available or can be prepared by known literature procedures, conversion to the corresponding N-protected-3-substituted pyrrolidine is preferably done by reaction with N-benzyl-N-(methoxymethyl)trimethylsilylmethylamine and a catalytic amount of trifluoroacetic acid in dichloromethane at −10° C. to the reflux temperature of the reaction mixture, and for 0.5 to 12 hours. Other solvents include acetonitrile, tetrahydrofuran, dioxane, chloroform, dichloroethane, toluene, and the like. Alternative catalysts include anhydrous potassium or cesium fluoride, tetra-n-butylammonium fluoride, trifluoromethanesulfonic acid, trimethylsilyl trifluoromethanesulfonate, and iodotrimethylsilane [cf. A. Hosomi, et al, Chem. Lett. 1117 (1984); Y. Terao, et al, Chem. Pharm. Bull. 33:2762 (1985)].

Reduction of the nitro or cyano substituents is best accomplished by catalytic hydrogenation with hydrogen gas. The preferred catalysts include Raney nickel and varying percentages of rhodium, platinum, or platinum oxide on an inert support such as carbon or alumina. Methanol, ethanol, tetrahydrofuran, acetic acid, and ethyl acetate, with or without the addition of water, ammonia, or hydrochloric acid, are used as solvent. The reaction is run at ambient temperature to 80°-90° C. for 0.5 to 24 hours. Alternatively, the reduction can be carried forward with a hydride reducing agent in an inert solvent. The preferred method employs lithium aluminum hydride in tetrahydrofuran at reflux for 2 to 12 hours.

The resulting amino or aminomethyl substituent may be reacted with an amino-protecting reagent such as acetic anhydride, acetyl chloride, trifluoroacetic anhydride, methyl trifluoroacetate, or di-tert-butyl dicarbonate, in the presence of a tertiary amine such as triethylamine, diisopropylethylamine, or pyridine, with or without an inert solvent such as an ether or chlorocarbon, in a temperature range of 0° C. to the reflux temperature of the reaction mixture, and for 6 to 72 hours. Preferred conditions are with di-tert-butyl dicarbonate and diisopropylethylamine in dichloromethane at room temperature for 12 hours.

The N-acetyl-, N-trifluoroacetyl-, or N-tert-butoxycarbonyl-protected compounds may be reacted with a proton abstractor such as sodium hydride or a similar agent, in a solvent such as tetrahydrofuran or dimethylformamide, at −20° C. to 80° C., followed by addition of a methylating agent like iodomethane or methyl trifluoromethanesulfonate, to give the corresponding N-methylated derivative. The trifluoroacetyl or tert-butoxycarbonyl group may be removed by acid- or base-catalyzed hydrolysis, preferably with sodium hydroxide or trifluoroacetic acid, respectively. Alternatively, the N-acetyl or N-tert-butoxycarbonyl-protected compound may be reacted directly with a hydride reducing agent in an inert solvent, preferably lithium aluminum hydride in tetrahydrofuran, at 25° C. to the reflux temperature of the mixture, for 1 to 20 hours, to afford the corresponding N-ethyl or N-methyl substituted derivative, respectively.

The compounds bearing an unprotected amino or aminomethyl group may also be dimethylated by reaction with aqueous formaldehyde in formic acid, at 0° C. to the reflux temperature of the reaction mixture, for 2 to 10 hours.

The above derivatives, whether bearing an amino-protecting group or not, are debenzylated via hydrogenolysis with hydrogen gas or a source of hydrogen such as ammonium formate, cyclohexene, or cyclohexadiene, using varying percentages of palladium on an inert support such as carbon, alumina, silica, or the like, preferably 20% palladium on carbon, in an inert solvent such as methanol, ethanol, tetrahydrofuran, acetic acid, or ethyl acetate, with or without the addition of hydrochloric acid. Alternatively, a non-hydrogenolytic debenzylation can be carried out consisting in reacting the N-benzyl derivative with a silyl-substituted chloro- or azidoformate, followed by treatment of the resulting carbamate with a desylating agent, such as a source of fluoride ion. This provides the corresponding 3-(aminomethylphenyl or pyridyl)pyrrolidines in a form suitable for coupling with a quinolone or naphthyridine substrate of Formula II.

DESCRIPTION OF SCHEME II

Alternatively, starting with a suitably N-protected-3-alkoxycarbonyl substituted pyrrolidine (Scheme II), conversion to a 3-(1,2,4-oxadiazol-5-yl) pyrrolidine may be accomplished by reaction with acetamide oxime or hydroxyguanidine sulfate, in the presence of a proton abstractor such as a metal hydride, sodium or potassium alkoxide, or sodium metal, in a solvent such as benzene, toluene, diethyl ether, tetrahydrofuran, diglyme, methanol, or ethanol, at 25° C. to the reflux temperature of the reaction mixture. Preferred conditions include sodium hydride in tetrahydrofuran at reflux or sodium metal in ethanol at reflux. Alternatively, reaction with aminoguanidine bicarbonate provides the corresponding 3-(1,2,4-triazol-5-yl) substituted pyrrolidine.

The 3-alkoxycarbonyl substituted pyrrolidine can be directly converted into other 3-heteroaryl substituted pyrrolidines using known art. This transformation may also be carried out via the corresponding carboxylic acid, available by selective hydrolysis of the ester with varying concentrations of sodium or potassium hydroxide in a water-alcohol mixture, at a temperature ranging from −10° C. to room temperature. The resulting acid can then be converted into the corresponding acid chloride by established literature procedures, for instance, by reaction with oxalyl chloride in dichloromethane at room temperature and in the presence of a catalytic amount of dimethylformamide. Treatment of the acid chloride with a substituted hydrazide, semicarbazide, or thiosemicarbazide, followed by ring closure under base- or acid-catalysis, affords the corresponding 3-heteroaryl substituted pyrrolidines.

The compounds of the invention display antibacterial activity when tested by the microtitration dilution method as described in Heifetz, et al, *Antimicr. Agents & Chemoth.* 6:124 (1974), which is incorporated herein by reference.

By use of the above reference method, the following minimum inhibitory concentration value (MICs in μg/mL) shown in Table I were obtained for representative compounds of the invention.

TABLE I

In Vitro Antibacterial Activity
Minimal Inhibitory Concentration MIC (μg/mL)

| Example No. | Enter. cloac. | E. coli Vogel | Kleb. pneu. | Prot. rettg. | Pseu. aeru. | S. aureus R | S | Streptococcus faec. | pneum. | pyog. |
|---|---|---|---|---|---|---|---|---|---|---|
| 1 | 0.1 | 0.1 | 0.2 | 0.4 | 1.6 | 0.05 | 0.013 | 0.05 | 0.025 | 0.025 |
| 6 | 0.05 | 0.05 | 0.05 | 0.1 | 0.8 | 0.013 | 0.006 | 0.025 | 0.006 | 0.006 |
| 7 | 0.05 | 0.05 | 0.1 | 0.1 | 0.8 | 0.025 | 0.006 | 0.013 | ≦0.003 | ≦0.003 |
| 8 | 0.05 | 0.05 | 0.1 | 0.2 | 0.8 | 0.013 | ≦0.003 | 0.013 | 0.006 | 0.013 |
| 11 | 0.1 | 0.1 | 0.2 | 0.2 | 0.8 | 0.013 | ≦0.003 | 0.013 | 0.013 | 0.013 |
| 13 | 0.2 | 0.2 | 0.4 | 0.8 | 1.6 | 0.05 | 0.013 | 0.05 | 0.05 | 0.05 |
| 14 | 0.2 | 0.2 | 0.4 | 0.4 | 1.6 | 0.013 | 0.006 | 0.025 | 0.013 | 0.013 |
| 15 | 0.2 | 0.2 | 0.4 | 0.4 | 1.6 | 0.013 | 0.006 | 0.025 | 0.013 | 0.013 |
| 17 | 0.1 | 0.1 | 0.2 | 0.2 | 0.8 | 0.006 | ≦0.003 | 0.05 | 0.05 | 0.05 |
| 21 | 0.1 | 0.1 | 0.2 | 0.2 | 0.8 | 0.006 | ≦0.003 | 0.025 | 0.025 | 0.025 |
| 22 | 0.1 | 0.1 | 0.2 | 0.2 | 1.6 | 0.006 | ≦0.003 | 0.05 | 0.025 | 0.025 |
| 25 | 0.2 | 0.2 | 0.4 | 0.4 | 3.1 | 0.006 | ≦0.003 | 0.05 | 0.05 | 0.05 |

TABLE I-continued

| | | In Vitro Antibacterial Activity Minimal Inhibitory Concentration MIC (μg/mL) | | | | | | | | |
|---|---|---|---|---|---|---|---|---|---|---|
| Example No. | Enter. cloac. | E. coli Vogel | Kleb. pneu. | Prot. rettg. | Pseu. aeru. | S. aureus R | S | Streptococcus faec. | pneum. | pyog. |
| 29 | 0.05 | 0.05 | 0.1 | 0.2 | 1.6 | 0.025 | 0.013 | 0.025 | 0.025 | 0.025 |

The compounds of the invention can be prepared and administered in a wide variety of oral, parenteral, and topical dosage forms. It will be obvious to those skilled in the art that the following dosage forms may comprise as the active component, either a compound of Formula I or a corresponding pharmaceutically acceptable salt of a compound of Formula I.

For preparing pharmaceutical compositions from the compounds described by this invention, inert, pharmaceutically acceptable carriers can be either solid or liquid. Solid form preparations include powders, tablets, dispersible granules, capsules, cachets, suppositories, and ointments. A solid carrier can be one or more substances which may also act as diluents, flavoring agents, solubilizers, lubricants, suspending agents, binders, or tablet disintegrating agents; it can also be an encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 to 10 to about 70 percent of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

Liquid form preparations include solutions, suspensions, and emulsions. As an example may be mentioned water or water-propylene glycol solutions for parenteral injection. Such solutions are prepared so as to be acceptable to biological systems (isotonicity, pH, etc). Liquid preparation can also be formulated in solution in aqueous polyethylene glycol solution. Aqueous solutions suitable for oral use can be prepared by dissolving the active component in water and adding suitable colorants, flavors, stabilizing, and thickening agents as desired. Aqueous suspension suitable for oral use can be made by dispersing the finely divided active component in water with viscous material, i.e., natural or synthetic gums, resins, methyl cellulose, sodium carboxymethyl cellulose, and other well-known suspending agents.

Ointment preparations contain heavy metal salts of a compound of Formula I with a physiologically acceptable carrier. The carrier is desirably a conventional water-dispersible hydrophilic or oil-in-water carrier, particularly a conventional semi-soft or cream-like water-dispersible or water soluble, oil-in-water emulsion which may be applied to an affected burn surface or infected surface with a minimum of discomfort. Suitable compositions may be prepared by merely incorporating or homogeneously admixing finely divided compounds with the hydrophilic carrier or base or ointment.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, powders in vials or ampules, and ointments in tubes or jars. The unit dosage form can also be a capsule, cachet, tablet, gel or cream itself or it can be the appropriate number of any of these packaged forms.

The quantity of active compound in a unit dose of preparation may be varied or adjusted from 1 mg to 100 mg according to the particular application and the potency of the active ingredient.

In therapeutic use as agents for treating bacterial infections the compounds utilized in the pharmaceutical method of this invention are administered at the initial dosage of about 3 mg to about 40 mg per kilogram daily. A daily dose range of about 6 mg to about 14 mg per kilogram is preferred. The dosages, however, may be varied depending upon the requirements of the patient, the severity of the condition being treated, and the compound being employed. Determination of the proper dosage for a particular situation is with the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The following nonlimiting examples illustrate methods for preparing the compounds of the invention.

PREPARATION OF STARTING PYRROLIDINES

EXAMPLE A

2-[1-(Phenylmethyl)-3-pyrrolidinyl]benzonitrile

A solution of N-benzyl-N-(methoxymethyl)trimethylsilylmethylamine (16.62 g, 70.0 mmol) in dichloromethane (15 mL) are added dropwise, over a 45-minute period, to a solution of 2-ethenylbenzonitrile (6.00 g, 46.0 mmol) and trifluoroacetic acid (0.57 g, 5.0 mmol) in dichloromethane (55 mL). The resulting solution was stirred at room temperature for an additional 10 to 15 minutes, and then heated with saturated aqueous sodium bicarbonate solution (ca 10–15 mL). The organic layer was decanted, washed with water, and dried over anhydrous magnesium sulfate. Filtration and concentration of the solution provided an orange oil which was chromatographed (silica-gel, hexanes-ethyl acetate 5:1) to afford the title compound (6.95 g, 58%) as a pale yellow oil.

$^1$H-NMR (300 MHz, CDCl$_3$): $\delta$ = 1.80–1.92 (1H, m), 2.43–2.55 (1H, m), 2.63–2.75 (2H, m), 2.88–2.96 (2H, m), 3.71 (2H, AB quartet, $J_{AB}$ = 13.0 Hz), 3.78–3.86 (1H, m), 7.25–7.41 (6H, m), 7.53–7.66 (3H, m).

EXAMPLE B

3-[1-(Phenylmethyl)-3-pyrrolidinyl]benzonitrile

Starting from 3-ethenylbenzonitrile (8.00 g, 62.0 mmol), a procedure analogous to that given in Example A provided the title compound (12.41 g, 76%) as a faint yellow oil after chromatography (silica gel, hexanes-ethyl acetate 2: 1 ).

$^1$H-NMR (250 MHz, CDCl$_3$): δ=1.75–1.89 (1H, m), 2.29–2.44 (1H, m), 2.54 (1H, dd, J=9.3, 6.5 Hz), 2.67–2.84 (2H, m), 2.93 (1H, dd, J=9.3, 7.7 Hz), 3.30–3.42 (1H, m), 3.67 (2H, AB quartet, J$_{AB}$=13.2 Hz), 7.22–7.39 (6H, m), 7.45–7.54 (2H, m), 7.58–7.59 (1H, m).

EXAMPLE C

4-[1-(Phenylmethyl)-3-pyrrolidinyl]benzonitrile

Starting from 4-ethenylbenzonitrile (8.80 g, 68.1 mmol), a procedure analogous to that given in Example A provided the title compound (13.59 g, 76%) as an off-yellow solid after recrystallization from ethyl acetate/hexanes, mp 78°–79° C.

$^1$H-NMR (250 MHz, CDCl$_3$): δ=1.79–1.92 (1H, m), 2.30–2.45 (1H, m), 2.56–2.62 (1H, m), 2.70–2.85 (2H, m), 2.96 (1H, dd, J=9.4, 7.9 Hz), 3.34–3.44 (1H, m), 3.69 (2H, s), 7.25–7.41 (7H, m), 7.55–7.59 (2H, m).

EXAMPLE D

2-[1-(Phenylmethyl)-3-pyrrolidinyl]pyridine

Starting from 2-ethenylpyridine (7.00 g, 66.6 mmol), a procedure analogous to that given in Example A provided the title compound (12.50 g, 79%) as a light orange oil after chromatography (silica gel, chloroform-methanol 20:1).

$^1$H-NMR (250 MHz, CDCl$_3$): δ=2.03–2.16 (1H, m), 2.27–2.41 (1H, m), 2.65 (1H, dd, J=9.2, 7.9 Hz), 2.69–2.76 (1H, m), 2.83–2.92 (1H, m), 3.08 (1H, dd, J=8.6, 7.9 Hz), 3.48–3.64 (1H, m), 3.69 (2H, s), 7.05–7.11 (1H, m), 7.16–7.38 (6H, m), 7.54–7.61 (1H, m), 8.53 (1H, d, J=4.9 Hz).

EXAMPLE E

3-[1-(Phenylmethyl)-3-pyrrolidinyl]pyridine

Starting from 3-ethenylpyridine ( 6.2 0 g, 59.0 mmol), a procedure analogous to that given in Example A provided the title compound (5.10 g, 36%) as an orange oil after chromatography (silica gel, chloroform-methanol 20:1).

$^1$H-NMR (250 MHz, CDCl$_3$): δ=1.80–1.94 (1H, m), 2.31–2.45 (1H, m), 2.58 (1H, dd, J=9.1, 7.0 Hz), 2.76–2.82 (2H, m), 2.96–3.03 (1H, m), 3.31–3.43 (1H, m), 3.70 (2H, s), 7.19–7.38 (6H, m), 7.64 (1H, dist. d, J=7.9 Hz), 8.43 (1H, d, J=4.7 Hz), 8.51 (1H, dist. d, J=2.1 Hz).

EXAMPLE F

4-[1-(Phenylmethyl)-3-pyrrolidinyl]pyridine

Starting from 4-ethenylpyridine (4.21 g, 40.0 mmol), a procedure analogous to that given in Example A provided the title compound (6.50 g, 68%) as a yellow oil after chromatography (silica gel, chloroform-methanol 20:1).

$^1$H-NMR (250 Hz, d$_6$-DMSO): δ=1.68–1.82 (1H, m) , 2.19–2.33 (1H, m), 2.48 (1H, dd, J=9.1, 6.5 Hz), 2.61 (1H, dd, J=16.0, 8.7 Hz), 2.66–2.76 (1H, m), 2.85 (1H, dist. t, J=8.6, 8.2 Hz), 3.26–3.38 (1H, m), 3.63 (2H, AB quartet, J$_{AB}$=13.1 Hz) , 7.22–7.34 (7H, m) , 8.45 (2H, d, J=5.4 Hz).

EXAMPLE G

3-Nitro-2-[1-(phenylmethyl)-3-pyrrolidinyl]pyridine

Starting from 2-ethenyl-3-nitropyridine (4.50 g, 30.0 mmol), a procedure analogous to that given in Example A provided the title compound (5.50 g, 65%) as a yellow oil after chromatography (silica gel, hexanes-ethyl acetate 1: 1 ).

$^1$H-NMR (300 MHz, CDCl$_3$): δ=2.20–2.45 (2H, m), 2.78–3.00 (3H, m), 3.15–3.27 (1H, m), 3.60–3.89 (2H, m), 4.02–4.11 (1H, m), 7.20–7.70 (6H, m), 8.08 (1H, dd, J=8.3, 1.7 Hz), 8.80 (1H, dd, J=4.8, 1.7 Hz).

EXAMPLE H

2-[1-(Phenylmethyl-3-pyrrolidinyl]-3-pyridinecarbonitrile

Starting from 2-ethenyl-3-pyridinecarbonitrile (3.90 g, 30.0 mmol), a procedure analogous to that given in Example A provided the title compound (4.78 g, 54%) as a yellow oil after chromatography (silica gel, hexanes-ethyl acetate 1:1).

$^1$H-NMR (300 MHz, CDCl$_3$): δ=2.15–2.37 (1H, m) , 2.32–2.46 (1H, m), 2.70–2.81 (2H, m), 2.90–3.00 (1H, m), 3.17 (1H, t, J=8.6 Hz), 3.74 (2H, AB quartet, J$_{AB}$=12.9 Hz), 3.98–4.09 (1H, m), 7.21–7.41 (6H, m), 7.88 (1H, dd, J=7.9, 1.8 Hz), 8.77 (1H, dd, J=4.9, 1.7 Hz).

EXAMPLE I

3-[1-(Phenylmethyl)-3-pyrrolidinyl]benzenemethanamine

A suspension of 3-[1-(phenylmethyl)-3-pyrrolidinyl]benzonitrile (11.90 g, 45.4 mmol) and Raney nickel (5.0 g) in methanol saturated with ammonia (100 mL) was hydrogenated in a Parr shaker at 3 atm. The resulting suspension was filtered through a pad of Celite and the filtrate concentrated to give an off-green liquid. This crude product was chromatographed (silica gel, chloroform-methanol 2:1) to give the title compound (10.12 g, 84%) as a colorless oil.

$^1$H-NMR (250 MHz, CDCl$_3$): δ=1.68–1.75 (2H, br. s), 1.83–1.97 (1H, m), 2.27–2.41 (1H, m), 2.51 (1H, dd, J=9.0, 8.1 Hz), 2.71 (1H, td, J=8.9, 5.9 Hz), 2.80–2.90 (1H, m), 3.01–3.08 (1H, m), 3.31–3.41 (1H, m), 3.69 (2H, AB quartet, J$_{AB}$=13.3 Hz) , 3.84 (2H, s), 7.11–7.39 (9H, m).

EXAMPLE J

4-[1-(Phenylmethyl)-3-pyrrolidinyl]benzenemethanamine

Starting from 4-[1-(phenylmethyl)-3-pyrrolidinyl]benzonitrile (8.28 g, 31.6 mmol), a procedure analogous to that given in Example I provided the title compound (8.42 g, 100%) as a yellow oil.

$^1$H-NMR (250 MHz, CDCl$_3$): δ=1.79–1.93 (1H, m), 2.00–2.15 (1H, m), 2.24–2.39 (2H, m), 2.48 (1H, dd, J=8.9, 8.1 Hz), 2.68 (1H, td, J=8.9, 5.9 Hz), 2.78–2.88 (1H, m), 3.02 (1H, dd, J=9.0, 8.0 Hz), 3.35 (1H, dt, J=17.3, 7.7, 7.5 Hz), 3.67 (2H, AB quartet, J$_{AB}$=13.3 Hz), 3.81 (2H, s), 7.21–7.38 (9H, m).

EXAMPLE K

1,1-Dimethylethyl[[3-[1-(phenylmethyl)-3-pyrrolidinyl]phenyl]methyl]carbamate A solution of 3-[1-(phenylmethyl)-3-pyrrolidinyl]benzenemethanamine (8.00 g, 30.0 mmol), di-tert-butyl dicarbonate (7.86 g, 36.0 mmol) and diisopropylethylamine (4.65 g, 36.0 mmol) in dichloromethane (300 mL) was stirred at room temperature for 18 hours. The solvent was removed and the residue was chromatographed (hexanes-ethyl acetate 1:1) to give the title compound (9.50 g, 86%) as a colorless oil.

$^1$H-NMR (300 MHz, CDCl$_3$): δ=1.47 (9H, s), 1.83–1.95 (1H, m), 2.23–2.40 (1H, m), 2.50 (1H, dd, J=9.0, 8.2 Hz), 2.72 (1H, td, J=9.0, 6.0 Hz), 2.83–2.91 (1H, m), 3.05 (1H, dd, J=9.2, 7.9 Hz), 3.37 (1H, dt, J=17.4, 7.7, 7.7 Hz), 3.70 (2H, s), 4.25–4.33 (2H, m), 4.82–4.95 (1H, br. s), 7.09–7.39 (9H, m).

EXAMPLE L

1,1-Dimethylethyl[[4-[1-(phenylmethyl)-3-pyrrolidinyl]phenyl]methyl]carbamate Starting from 4-[1-(phenylmethyl)-3-pyrrolidinyl]benzenemethanamine (8.00 g, 30.0 mmol), a procedure analogous to that given in Example K provided the title compound (9.80 g, 89%) as a faint yellow oil.

$^1$H-NMR (250 MHz, CDCl$_3$): δ=1.46 (9H, s), 1.79–1.90 (1H, m), 2.23–2.39 (1H, m), 2.47 (1H, dd, J=8.9, 8.0 Hz), 2.69 (1H, td, J=8.8, 5.9 Hz), 2.77–2.87 (1H, m), 3.01 (1H, dd, J=8.9, 8.0 Hz), 3.27–3.41 (1H, m), 3.66 (2H, s), 4.25–4.28 (2H, m), 4.78–4.83 (1H, m), 7.17–7.37 (9H, m).

EXAMPLE M

2-(3-Pyrrolidinyl)benzenemethanamine

A suspension of 2-[1-(phenylmethyl)-3-pyrrolidinyl]benzonitrile (6.98 g, 26.6 mmol), 20% palladium on charcoal catalyst (4.0 g), and concentrated hydrochloric acid (4.6 mL) in methanol (200 mL) was hydrogenated in a Parr apparatus at 3 atm. The suspension was then filtered through a pad of Celite and the filtrate concentrated to give the dihydrochloride salt of the title compound (6.40 g, 97%) as an off-white solid.

$^1$H-NMR (250 MHz, d$_6$-DMSO): δ=1.86–1.97 (1H, m), 2.32–2.42 (1H, m), 2.97–3.08 (1H, m), 3.10–3.23 (1H, m), 3.35–3.42 (1H, m), 3.59–3.74 (2H, m), 4.08–4.16 (2H, m), 7.30–7.60 (4H, m), 8.50–8.65 (3H, m), 9.44–9.60 (1H, m), 9.70–9.85 (1H, m).

EXAMPLE N

1,1-Dimethylethyl[[3-(3-pyrrolidinyl)phenyl]methyl]carbamate

A suspension of 1,1-dimethylethyl[[3-[1-(phenylmethyl)-3-pyrrolidinyl]phenyl]methyl]carbamate (4.50 g, 12.3 mmol) and 20% palladium on charcoal catalyst (0.30 g) in methanol (100 mL) was hydrogenated in a Parr apparatus at 3 atm. The suspension was filtered through a pad of Celite and the filtrate concentrated to give an orange oil. This oil was chromatographed (silica gel, dichloromethanemethanol 1:1 containing 1% ammonia) to give the title compound (2.99 g, 88%) as a pale yellow oil.

$^1$H-NMR (250 MHz, CDCl$_3$): δ=1.46 (9H, s), 1.80–1.93 (1H, m), 2.19–2.35 (1H, m), 2.86 (1H, dd, J=10.5, 8.2 Hz), 3.05–3.29 (3H, m), 3.38 (1H, dd, J=10.5, 7.7 Hz), 4.26–4.32 (2H, m), 4.80–4.94 (1H, m), 7.13–7.18 (3H, m), 7.23–7.32 (1H, m).

EXAMPLE O

1,1-Dimethylethyl[[4-(3-pyrrolidinyl)phenyl]methyl]carbamate

Starting from 1,1-dimethylethyl[[4-[1-(phenylmethyl)-3-pyrrolidinyl]phenyl]methyl]carbamate (5.17 g, 14.1 mmol), a procedure analogous to that given in Example N provided the title compound (3.47 g, 89%) as a pale yellow oil.

$^1$H-NMR (250 MHz, CDCl$_3$): δ=1.46 (9H, S), 1.78–1.91 (1H, m), 2.19–2.27 (1H, m), 2.83 (1H, dd, J=10.4, 8.2 Hz), 3.04–3.28 (3H, m), 3.36 (1H, dd, J=10.4, 7.6 Hz), 4.26–4.30 (2H, m), 4.80–4.90 (1H, m), 7.19–7.22 (4H, m).

EXAMPLE P

N-Methyl-3-[1-(phenylmethyl)-3-pyrrolidinyl]benzenemethanamine

A solution of 1,1-dimethylethyl[[3-[1-(phenylmethyl)-3-pyrrolidinyl]phenyl]methyl]carbamate (4.50 g, 12.3 mmol), in anhydrous tetrahydrofuran (100 mL) was added portionwise to a stirred suspension of lithium aluminum hydride (1.28 g, 34.0 mmol) in dry tetrahydrofuran (100 mL). The resulting suspension was heated at reflux for 4 hours, then allowed to cool to room temperature, and quenched by addition of saturated aqueous ammonium sulfate solution (50 mL) and water (100 mL). The precipitated solids were filtered through a pad of Celite, washed with methanol, and the filtrate and washings concentrated under reduced pressure. The residue was taken up in water and extracted with dichloromethane (4×50 mL). The organic extracts were combined, washed with brine, dried over anhydrous magnesium sulfate, filtered, and concentrated to an orange oil. This oil was redissolved in dichloromethane and treated with hydrogen chloride for 30–60 min. Evaporation of the solvent gave an oil which was chromatographed (silica gel, dichloromethane-methanol 5:1) to give the hydrochloride salt (ca. 4.00 g, 100%) of the title compound as a light orange oil.

$^1$H-NMR (300 MHz, CDCl$_3$): δ=1.86–1.97 (1H, m), 2.05–2.14 (1H, m), 2.29–2.41 (1H, m), 2.47–2.54 (1H, m), 2.48 (3H, s), 2.66–2.75 (1H, m), 2.82–2.90 (1H, m), 3.06 (1H, dd, J=9.0, 7.9 Hz), 3.33–3.43 (1H, m), 3.70 (2H, s), 7.75 (2H, s), 7.15–7.40 (9H, m).

EXAMPLE Q

N-Methyl-4-[1-(phenylmethyl)-3-pyrrolidinyl]benzenemethanamine

Starting from 1,1-dimethylethyl[[4-[1-(phenylmethyl)-3-pyrrolidinyl]phenyl]methyl]carbamate (5.15 g, 14.0 mmol), a procedure analogous to that given in Example P provided the title compound (4.07 g, 92%) as an off-white solid.

$^1$H-NMR (300 MHz, CDCl$_3$): δ=1.81–1.92 (1H, m), 2.27–2.38 (1H, m), 2.45 (3H, s), 2.46–2.53 (1H, m), 2.66–2.74 (1H, m), 2.79–2.88 (1H, m), 2.99–3.04 (1H, m), 3.30–3.41 (1H, m), 3.68 (2H, s), 3.77 (2H, s), 4.02–4.11 (1H, br. s), 7.23–7.38 (9H, m).

EXAMPLE R

N-Methyl-3-(3-pyrrolidinyl)benzenemethanamine

Starting from N-methyl-3-[1-(phenylmethyl)-3-pyrrolidinyl]benzenemethanamine (4.43 g, 15.8 mmol), a procedure analogous to that given in Example M provided the title compound (1.39 g, 46%) as a pale yellow oil.

$^1$H-NMR (300 MHz, CDCl$_3$): δ=1.79–1.91 (1H, m), 2.17–2.28 (1H, m), 2.41 (3H, s), 2.82–2.90 (1H, m), 3.04–3.28 (3H, m), 3.32–3.39 (1H, m), 3.68 (2H, s), 7.08–7.27 (4H, m).

EXAMPLE S

N-Methyl-4-(3-pyrrolidinyl)benzenemethanamine

Starting from N-methyl-4-[1-(phenylmethyl)-3-pyrrolidinyl]benzenemethanamine (3.96 g, 14.1 mmol), a procedure analogous to that given in Example M provided the title compound (1.61 g, 60%) as a pale yellow oil.

$^1$H-NMR (250 MHz, d$_6$-DMSO): δ=1.60–1.75 (1H, m), 2.08–2.21 (1H, m), 2.22 (3H, s), 2.56–2.63 (1H, m), 2.83–3.04 (2H, m), 3.07–3.22 (2H, m), 3.56 (2H, s), 7.18–7.25 (4H, m).

EXAMPLE T

N,N-Dimethyl-3-[1-(phenylmethyl)-3-pyrrolidinyl]-benzenemethanamine

A solution of 3-[1-(phenylmethyl)-3-pyrrolidinyl]-benzenemethanamine (1.65 g, 6.2 mmol), sodium formate (1.70 g, 25.0 mmol), 37% aqueous formaldehyde (62 mL) and 90% aqueous formic acid (62 mL) was heated at reflux for 3.5 hours. The solvent was evaporated to give a mixture of a white solid and a yellow liquid. The solid was filtered and washed with methanol and ether. The filtrate and washings were combined and concentrated under reduced pressure. The resulting residue was taken up in water (30 mL), and the solution was made basic with concentrated ammonia and extracted with dichloromethane (3×50 mL). The organic extracts were washed with water, dried over anhydrous magnesium sulfate, and concentrated to a yellow oil. This oil was chromatographed (silica gel, dichloromethane-methanol 10:1) to give the title compound (1.35 g, 74%) as a colorless oil.

$^1$H-NMR (250 MHz, d$_6$-DMSO): δ=1.67–1.80 (1H, m), 2.12 (6H, s), 2.18–2.30 (1H, m), 2.43 (1H, dd, J=9.0, 7.1 Hz), 2.63–2.69 (2H, m), 2.86 (1H, dd, J=9.0, 8.0 Hz), 3.23–3.33 (1H, m), 3.34 (2H, s), 3.63 (2H, AB quartet, J$_{AB}$=13.0 Hz), 7.05–7.09 (1H, m), 7.13–7.33 (8H, m).

EXAMPLE U

N,N-Dimethyl-3-(3-pyrrolidinyl)benzenemethanamine

Starting from N,N-dimethyl-3-[1-(phenylmethyl)-3-pyrrolidinyl]benzenemethanamine (1.33 g, 4.5 mmol), a procedure analogous to that given in Example M provided the title compound (0.14 g, 15%), as a pale yellow oil.

$^1$H-NMR (250 MHz, CDCl$_3$): δ=1.81–1.92 (1H, m), 2.20–2.29 (1H, m), 2.24 (6H, s), 2.89 (1H, dd, J=10.5, 8.3 Hz), 3.07–3.30 (3H, m), 3.36–3.42 (3H, m), 7.12–7.29 (4H, m).

EXAMPLE V

2-(3-Pyrrolidinyl)pyridine

To a suspension of 2-[1-(phenylmethyl)-3-pyrrolidinyl]pyridine (7.15 g, 30.0 mmol) and 10% palladium on charcoal catalyst (1.90 g) in methanol (120 mL) was added dropwise a solution of ammonium formate (7.57 g, 120 mmol) in water (30 mL). The mixture was heated at reflux for 30 minutes, allowed to cool to room temperature, and filtered. The filtrate was concentrated under reduced pressure, the residue was taken up in water (10 mL), and the solution was made basic with concentrated ammonia and extracted with dichloromethane (4×15 mL). The organic extracts were combined, dried over anhydrous potassium carbonate, and concentrated to a yellow oil. This crude product was chromatographed (silica gel, chloroform-methanol-ammonia 75:25:5) to give the title compound (3.33 g, 75%) as a faint yellow liquid.

$^1$H-NMR (300 MHz, d$_6$-DMSO): δ=1.80–1.92 (1H, m), 2.02–2.13 (1H, m), 2.75–3.02 (3H, m), 3.11–3.17 (1H, m), 3.22–3.32 (1H, m), 7.16–7.20 (1H, m), 7.28 (1H, d, J=7.8 Hz), 7.67 (1H, d, J=7.7 Hz), 8.48 (1H, d, J=4.9 Hz).

EXAMPLE W

3-(3-Pyrrolidinyl)pyridine

Starting from 3-[1-(phenylmethyl)-3-pyrrolidinyl]pyridine (5.00 g, 21.0 mmol), a procedure analogous to that described in Example V provided the title compound (2.15 g, 69%) as a pale orange oil.

$^1$H-NMR (250 MHz, d$_6$-DMSO): δ=1.60–1.75 (1H, m), 2.08–2.29 (1H, m), 2.58–2.69 (1H, m), 2.85–3.04 (2H, m), 3.07–3.36 (2H, m), 7.31 (1H, dd, J=7.9, 4.9 Hz), 7.69 (1H, d, J=7.9 Hz), 8.39 (1H, d, J=4.9 Hz), 8.48 (1H, s).

EXAMPLE X

4-(3-Pyrrolidinyl)pyridine

Starting from 4-[1-(phenylmethyl)-3-pyrrolidinyl]-pyridine (5.90 g, 24.7 mmol), a procedure analogous to that described in Example V provided the title compound (3.00 g, 66%) as an orange oil.

$^1$H-NMR (250 MHz, d$_6$-DMSO): δ=1.86–2.02 (1H, m), 2.36–2.45 (1H, m), 3.09–3.23 (2H, m), 3.35–3.49 (1H, m), 3.53–3.68 (2H, m), 7.51 (2H, d, J=5.9 Hz), 8.58 (2H, d, J=5.9 Hz), 9.80–10.00 (2H, m).

EXAMPLE Y

2-(3-Pyrrolidinyl)-3-pyridinamine

Starting from 3-nitro-2-[1-(phenylmethyl)-3-pyrrolidinyl]pyridine (5.55 g, 19.6 mmol), a procedure analogous to that given in Example V provided the title compound (1.70 g, 53%) as a yellow oil.

$^1$H-NMR (300 MHz, CDCl$_3$): δ=1.97–2.09 (1H, m), 2.11–2.40 (1H, m), 2.60–2.82 (1H, m), 2.89 (1H, dt, J=10.5, 8.0, 8.0 Hz), 3.11 (1H, dd, J=10.7, 8.0 Hz), 3.18–3.29 (2H, m), 3.36–3.45 (1H, m), 4.00–4.40 (2H, m), 6.86–6.93 (2H, m), 7.87–7.90 (1H, m).

EXAMPLE Z

2-[1-(Phenylmethyl)-3-pyrrolidinyl]-3-pyridinemethanamine

Starting from 2-[1-(phenylmethyl)-3-pyrrolidinyl]-3-pyridinecarbonitrile (4.28 g, 16.3 mmol), a procedure analogous to that given in Example I provided the title compound (4.20 g, 97%) as a yellow oil.

¹H-NMR (300 MHz, CDCl₃): δ=1.63–1.74 (1H, m), 1.93–2.09 (1H, m), 2.17–2.31 (1H, m), 2.61–2.71 (1H, m), 2.98–3.16 (1H, m), 3.22–3.34 (1H, m), 3.64–3.80 (2H, m), 3.89–3.94 (1H, m), 4.16–4.29 (2H, m), 7.07–7.12 (1H, m), 7.20–7.40 (3H, m), 7.49–7.56 (1H, m), 7.58–7.66 (1H, m), 7.68–7.74 (1H, m), 8.40–8.53 (1H, m).

EXAMPLE AA 2-(3-Pyrridinyl)-3-pyridinemethanamine

Starting from 2-[1-(phenylmethyl)-3-pyrrolidinyl]-3-pyridinemethanamine (4.10 g, 15.3 mmol), a procedure analogous to that given in Example M provided the title compound (1.50 g, 56%) as a yellow oil.

¹H-NMR (300 MHz, CDCl₃): δ=1.81–1.95 (1H, m), 1.99–2.10 (1H, m), 2.30 (3H, br. s), 2.79–2.89 (1H, m), 3.01–3.15 (3H, m), 3.42–3.52 (1H, m), 3.79 (2H, s), 6.95 (1H, dd, J=7.6, 4.8 Hz), 7.48 (1H, d, J=7.6 Hz), 8.27 (1H, d, J=4.8 Hz).

PREPARATION OF SUBSTITUTED QUINOLONES AND NAPHTHYRIDONES

EXAMPLE 1

7-[3-[2-(Aminomethyl)phenyl]-1-pyrrolidinyl]-1-cyclopropyl-6-fluoro-1,4-dihydro-4-oxo-1,8-naphthyridine-3-carboxylic acid A suspension of 7-chloro-1-cyclopropyl-6-fluoro-1,4-dihydro-4-oxo-1,8-naphthyridine-3-carboxylic acid (1.13 g, 4.0 mmol), 2-(3-pyrrolidinyl)benzenemethanamine (1.25 g, 5.0 mmol), and a diisopropylethylamine (2.07 g, 16.0 mmol) in acetonitrile (50 mL) was heated at gentle reflux for 24 hours. The suspension was allowed to cool to room temperature; the precipitated solids were filtered, washed successively with cold acetonitrile and ether, and dried in vacuo to give the title compound (0.73 g, 43%) as a white solid, after recrystallization from methanol, mp 226°–228° C.

¹H-NMR (250 MHz, TFA): δ=1.21–1.38 (2H, m), 1.42–1.62 (2H, m), 2.28–2.48 (1H, m), 2.50–2.76 (1H, m), 3.90–4.19 (4H, m), 4.30–4.79 (2H, m), 4.65 (2H, br. s), 7.41–7.62 (4H, m), 8.11 (1H, d, J=11.6 Hz), 9.16 (1H, s), 11.60 (1H, br. s).

EXAMPLE 2

7-[3-[2-(Aminomethyl)phenyl]1-pyrrolidinyl]-1-cyclopropyl-6-fluoro-1,4-dihydro-4-oxo-3-quinolinecarboxylic acid Starting from 1-cyclopropyl-6,7-difluoro-1,4-dihydro-4-oxo-3-carboxylic acid (1.06 g, 4.0 mmol), and 2-(3-pyrrolidinyl)benzenemethanamine, a procedure analogous to that given in Example 1 provided the title compound (1.08 g, 64%) as a beige solid, mp 245°–247° C.

¹H-NMR (250 MHz, TFA): δ=1.30–1.41 (2H, m), 1.58–1.69 (2H, m), 2.32–2.52 (1H, m), 2.56–2.69 (1H, m), 3.85–4.19 (5H, m), 4.21–4.40 (1H, m), 4.59–4.78 (2H, m), 7.30–7.60 (5H, m), 8.13 (1H, d, J=13.4 Hz), 9.17 (1H, s), 11.63 (1H, br. s).

EXAMPLE 3

5-Amino-7-[3-[2-(aminomethyl)phenyl]-1-pyrrolidinyl]-1-cyclopropyl-6,8-difluoro-1,4-dihydro-4-oxo-3-quinolinecarboxylic acid Starting from 5-amino-1-cyclopropyl-6,7,8-trifluoro-1,4-dihydro-4-oxo-3-quinolinecarboxylic acid (1.00 g, 4.0 mmol) and 2-(3-pyrrolidinyl)benzenemethanamine, a procedure analogous to that given in Example 1 provided the title compound (0.65 g, 48%) as a bright yellow solid, mp 164°–165° C.

¹H-NMR (250 MHz, TFA): δ=1.30–1.60 (4H, m), 2.32–2.48 (1H, m), 2.51–2.65 (1H, m), 3.90–4.48 (6H, m), 4.60–4.70 (2H, m), 7.43–7.61 (4H, m), 9.17 (1H, s), 11.61 (1H, br. s).

EXAMPLE 4

7-[3-[2-(Aminomethyl)phenyl]-1-pyrrolidinyl]-1-cyclopropyl-6-fluoro-1,4-dihydro-4-oxo-8(trifluoromethyl)-3-quinolinecarboxylic acid Starting from 1-cyclopropyl-6,7-difluoro-1,4-dihydro-4-oxo-8-trifluoromethyl-3-quinolinecarboxylic acid (1.00 g, 3.0 mmol) and 2-(3-pyrrolidinyl)benzenemethanamine, a procedure analogous to that given in Example 1 provided the title compound.

¹H-NMR (250 MHz, TFA): δ=0.97–1.14 (1H, m), 1.16–1.39 (1H, m), 1.45–1.73 (2H, m), 2.10–2.75 (2H, m), 3.82–4.04 (1H, m), 4.05–4.80 (7H, m), 7.20–7.65 (4H, m), 8.07 (1H, d, J=13.4 Hz), 9.35 (1H, s).

EXAMPLE 5

7-[3-[2-(Aminomethyl)phenyl]-1-pyrrolidinyl]-1-cyclopropyl-6-fluoro-1,4-dihydro-8-methoxy-4-oxo-3-quinolinecarboxylic acid Starting from difluoroborane 1-cyclopropyl-6,7-difluoro-1,4-dihydro-8-methoxy-4-oxo-3-quinolinecarboxylate (1.13 g, 3.3 mmol) and 2-(3-pyrrolidinyl)benzenemethanamine, a procedure analogous to that given in Example 1, provided the fluoroborate ester of the title compound.

A suspension of the above fluoroborate ester and triethylamine (7.26 g, 71.7 mmol) in ethanol-ester 10:1 (110 mL) was heated at gentle reflux for 17 hours. The solvent was removed under reduced pressure and the residue was chromatographed (silica gel, choloroform-methanol-ammonia 75:25:5) to give the title compound (0.37 g, 73%) as a beige solid, mp 170°–174° C.

¹H-NMR (250 MHz, TFA): δ=1.20–1.36 (2H, m), 1.45–1.63 (2H, m), 2.62–2.81 (2H, m), 4.05 (3H, s), 4.17–4.61 (6H, m), 4.68 (2H, m), 7.41–7.65 (4H, m), 8.32 (1H, d, J=12.0 Hz), 9.47 (1H, s), 11.62 (1H, br. s).

EXAMPLE 6

7-[3-[3-(Aminomethyl)phenyl]-1-pyrrolidinyl]-1-cyclopropyl-6-fluoro-1,4-dihydro-4-oxo-1,8-naphthyridine-3-carboxylic acid A suspension of 7-chloro-1-cyclopropyl-6-fluoro-1,4-dihydro-4-oxo-1,8-naphthyridine-3-carboxylic acid (0.85 g, 3.0 mmol), 1,1-dimethyl[[3-(3-pyrrolidinyl)phenyl]methyl]carbamate (1.00 g, 3.6 mmol), and diisopropylethylamine (1.55 g, 12.0 mmol) in acetonitrile (50 mL) was heated at gentle reflux for 23 hours. The suspension was allowed to cool to room temperature; the precipitated solids were filtered, washed with cold methanol, ether, and dried in vacuo at 40° C. to give 1-cyclopropyl-7-[3-[3-[[(1,1-dimethylethoxy)carbonyl]amino]phenyl]-1-pyrrolidinyl]-6-fluoro-1,4-dihydro-4-oxo-1,8-naphthyridine-3-carboxylic acid (1.33 g, 85%) as an off-white solid, mp 210°–211° C.

¹H-NMR (250 MHz, d₆-DMSO+heat): δ=1.02–1.19 (4H, m), 1.38 (9H, s), 2.03–2.20 (1H, m), 2.32–2.43 (1H, m), 3.42–3.98 (4H, m), 4.02–4.19 (3H, m), 4.21–4.36 (1H, m), 7.13 (1H, d, J=7.1 Hz), 7.22–7.41 (4H, m), 7.95 (1H, d, J=12.6 Hz), 8.54 (1H, s), 15.40 (1H, br.s).

A solution of the above N-Boc protected compound (1.15 g, 2.2 mmol) and 6 N hydrochloric acid (20 mL) in acetone (50 mL) was heated at gentle reflux for 24 hours, and then concentrated under reduced pressure. The residue was dissolved in a small amount of methanol and the solution poured onto a large excess of ether; the precipitated solid was filtered, washed with isopropanol and ether, and dried in vacuo at 40° C. to give the title compound (0.94 g) as a yellow solid, mp 274°–276° C.

$^1$H-NMR (250 MHz, TFA): δ=1.20–1.28 (2H, m), 1.31–1.40 (2H, m), 2.23–2.54 (1H, m), 2.58–2.78 (1H, m), 3.60–3.82 (1H, m), 3.95–4.20 (3H, m), 4.35–4.78 (4H, m), 7.40–7.60 (4H, m), 8.09 (1H, d, J=11.6 Hz), 9.14 (1H, s), 11.61 (1H, br. s).

EXAMPLE 7

7-[3-[3-(Aminomethyl)phenyl]-1-pyrrolidinyl]-1-cyclopropyl-6-fluoro-1,4-dihydro-4-oxo-3-quinolinecarboxylic acid Starting from 1-cyclopropyl-6,7-difluoro-1,4-dihydro-4-oxo-3-quinolinecarboxylic acid (0.80 g, 3.0 mmol), a procedure analogous to that given in Example 6 provided the title compound (0.98 g) as a bright yellow solid, mp 250°–253° C.

$^1$H-NMR (250 MHz, TFA): δ=1.32–1.45 (2H, m), 1.58–1.68 (2H, m), 2.30–2.48 (1H, m), 2.57–2.73 (1H, m), 3.65–3.82 (1H, m), 3.83–4.21 (4H, m), 4.25–4.38 (1H, m), 4.46 (2H, s), 7.40–7.60 (5H, m), 8.13 (1H, d, J=13.4 Hz), 9.17 (1H, s), 11.60 (1H, br. s).

EXAMPLE 8

5-Amino-7-[3-[3-(aminomethyl)phenyl]-1-pyrrolidinyl]-1-cyclopropyl-6,8-difluoro-1,4-dihydro-4-oxo-3-quinolinecarboxylic acid Starting from 5-amino-1-cyclopropyl-6,7,8-trifluoro-1,4-dihydro-4-oxo-3-quinolinecarboxylic acid (0.85 g, 2.5 mmol), a procedure analogous to that given in Example 6 provided the title compound (0.40 g) as a yellow solid after recrystallization from methanol-isopropanol, mp 246°–248° C. (dec).

$^1$H-NMR (250 MHz, TFA): δ=1.30–1.60 (4H, m), 2.33–2.51 (1H, m), 2.57–2.69 (1H, m), 3.65–3.81 (1H, m), 4.10–4.50 (7H, m), 7.42–7.60 (4H, m), 9.19 (1H, s), 11.60 (1H, br. s).

EXAMPLE 9

7-[3-[4-(Aminomethyl)phenyl]-1-pyrrolidinyl]-1-cyclopropyl-6-fluoro-1,4-dihydro-4-oxo-1,8-naphthyridine-3-carboxylic acid Starting from 7-chloro-1-cyclopropyl-6-fluoro-1,4-dihydro-4-oxo-1,8-naphthyridine-3-carboxylic acid (0.94 g, 3.3 mmol) and 1,1-dimethylethyl[[4-(3-pyrrolidinyl)phenyl]methyl]carbamate, a procedure analogous to that given in Example 6 provided the title compound (1.30 g) as an off-white solid, mp 268°–272° C.

$^1$H-NMR (250 MHz, TFA): δ=1.22–1.38 (2H, m), 1.43–1.60 (2H, m), 2.25–2.53 (1H, m), 2.57–2.68 (1H, m), 3.61–3.80 (1H, m), 3.97–4.20 (3H, m), 4.38–4.70 (4H, m), 7.49 (2H, d, J=7.9 Hz), 7.54 (2H, d, J=7.9 Hz), 8.09 (1H, d, J=10.4 Hz), 9.15 (1H, s), 11.60 (1H, hr. s).

EXAMPLE 10

7-[3-[4-Aminomethyl)phenyl]-1-pyrrolidinyl]-1-cyclopropyl-6-fluoro-1,4-dihydro-4-oxo-3-quinolinecarboxylic acid Starting from 1-cyclopropyl-6,7-difluoro-1,4-dihydro-4-oxo-3-quinolinecarboxylic acid ( 0.88 g, 3.3 mmol) and 1,1-dimethylethyl[[4-(3-pyrrolidinyl) -phenyl]methyl]carbamate, a procedure analogous to that given in Example 6 provided the title compound (1.02 g) as a bright yellow solid, mp 268°–272° C.

$^1$H-NMR (250 MHz, TFA): δ=1.10–1.16 (2H, m), 1.26–1.34 (2H, m), 2.14–2.25 (1H, m), 2.37–2.50 (1H, m), 3.54–3.67 (2H, m), 3.68–3.87 (3H, m), 4.00–4.10 (3H, m), 7.10 (1H, d, J=7.9 Hz), 7.48 (4H, br. s), 7.80 (1H, d, J=14.0 Hz), 8.58 (1H, s), 15.32 (1H, hr. s).

EXAMPLE 11

5-Amino-7-[3-[4-(aminomethyl)phenyl]-1-pyrrolidinyl]-1-cyclopropyl-6,8-difluoro-1,4-dihydro-4-oxo-3-quinolinecarboxylic acid Starting from 5-amino-1-cyclopropyl-6,7,8-trifluoro-1,4-dihydro-4-oxo-3-quinolinecarboxylic acid (0.95 g, 3.2 mmol) and 1,1-dimethylethyl[[4-(3-pyrrolidinyl)-phenyl]methyl]carbamate, a procedure analogous to that given in Example 6 provided the title compound (0.75 g) as a yellow solid, mp 225°–227° C.

$^1$H-NMR (250 MHz, TFA): δ=1.26–1.60 (4H, m), 2.27–2.48 (1H, m), 2.52–2.65 (1H, m), 3.62–3.80 (1H, m), 4.11–4.50 (7H, m), 7.40–7.60 (4H, m), 9.19 (1H, s), 11.58 (1H, br. s).

EXAMPLE 12

1-Cyclopropyl-6-fluoro-1,4-dihydro-7-[3-[3-[(methylamino)methyl]phenyl]-1-pyrrolidinyl]-4-oxo-3-quinolinecarboxylic acid Starting from 1-cyclopropyl-6,7-difluoro-1,4-dihydro-4-oxo-3-quinolinecarboxylic acid (0.93 g, 3.5 mmol) and N-methyl-3-(3-pyrrolidinyl)benzenemethanamine, a procedure analogous to that given in Example 1 provided the title compound (1.38 g, 91%) as a white solid, mp 239°–240° C.

$^1$H-NMR (250 MHz, TFA): δ=1.32–1.41 (2H, m), 1.58–1.67 (2H, m), 2.29–2.48 (1H, m), 2.59–2.69 (1H, m), 2.99–3.05 (3H, m), 3.61–3.79 (1H, m), 3.81–4.20 (4H, m), 4.25–4.44 (3H, m), 7.32–7.59 (5H, m), 8.12 (1H, d, J=13.4 Hz), 9.16 (1H, s), 11.63 (1H, br. s).

EXAMPLE 13

5-Amino-1-cyclopropyl-6,8-difluoro-1,4-dihydro-7-[3-[3-[(methylamino)methyl]phenyl]-1-pyrrolidinyl]-4-oxo-3-quinolinecarboxylic acid Starting from 5-amino-1-cyclopropyl-6,7,8-trifluoro-1,4-dihydro-4-oxo-3-quinolinecarboxylic acid (0.52 g, 1.7 mmol) and N-methyl-3-(3-pyrrolidinyl)benzenemethanamine, a procedure analogous to that given in Example 1 provided the title compound (0.44 g, 55%) as a yellow solid, mp>270° C.

$^1$H-NMR (250 MHz, TFA): δ=1.25–1.62 (4H, m), 2.30–2.49 (1H, m), 2.52–2.69 (1H, m), 2.99–3.07 (3H, m), 3.65–3.90 (1H, m), 4.10–4.45 (7H, m), 7.40–7.60 (4H, m), 9.26 (1H, s), 11.58 (1H, br. s).

EXAMPLE 14

1-Cyclopropyl-6-fluoro-1,4-dihydro-7-[3-[4-[(methylamino)methyl]phenyl]-1-pyrrolidinyl]-4-oxo-3-quinolinecarboxylic acid Starting from 1-cyclopropyl-6,7-difluoro-1,4-dihydro-4-oxo-3-quinolinecarboxylic acid (0.80 g, 3.0 mmol) and N-methyl-4-(3-pyrrolidinyl)benzenemethanamine, a procedure analogous to that given in Example 1 provided the title compound (1.11 g, 85%) as an off-white solid, mp 235°–237° C.

$^1$H-NMR (250 MHz, TFA): $\delta$=1.33–1.39 (2H, m), 1.58–1.64 (2H, m), 2.30–2.47 (1H, m), 2.58–2.68 (1H, m), 3.00–3.05 (3H, m), 3.68–3.79 (1H, m), 3.81–4.20 (4H, m), 4.23–4.41 (3H, m), 7.20–7.40 (1H, m), 7.51 (4H, br. s), 8.12 (1H, br. d, J=13.4 Hz), 9.16 (1H, s), 11.65 (1H, br. s).

EXAMPLE 15

5-Amino-1-cyclopropyl-6,8-difluoro-1,4-dihydro-7-[3-[4-[(methylamino)methyl]phenyl]-1-pyrrolidinyl]-4-oxo-3-quinolinecarboxylic acid Starting from 5-amino-1-cyclopropyl-6,7,8-trifluoro-1,4-dihydro-4-oxo-3-quinolinecarboxylic acid (0.89 g, 3.0 mmol) and N-methyl-4-(3-pyrrolidinyl)benzenemethanamine, a procedure analogous to that given in Example 1 provided the title compound (0.71 g, 51%) as a yellow solid, mp 201°–205° C.

$^1$H-NMR (250 MHz, TFA): $\delta$=1.30–1.39 (2H, m), 1.45–1.54 (2H, m), 2.28–2.47 (1H, m), 2.53–2.68 (1H, m), 2.99–3.06 (3H, m), 3.68–3.80 (1H, m), 4.08–4.40 (7H, m), 7.22–7.40 (1H, m), 7.52 (4H, br. s), 9.17 (1H, s), 11.62 (1H, br. s).

EXAMPLE 16

1-Cyclopropyl-6-fluoro-1,4-dihydro-4-oxo-7-[3-(2-pyridinyl)-1-pyrrolidinyl]-1,8-naphthyridine-3-carboxylic acid Starting from 7-chloro-1-cyclopropyl-6-fluoro-1,4-dihydro-4-oxo-1,8-naphthyridine-3-carboxylic acid (1.33 g, 4.7 mmol) and 2-(3-pyrrolidinyl)pyridine, a procedure analogous to that given in Example 1 provided the title compound (1.64 g, 88%) as an off-white solid, mp 203°–204° C.

$^1$H-NMR (250 MHz, TFA): $\delta$=1.22–1.38 (2H, m), 1.42–1.60 (2H, m), 2.47–2.73 (1H, m), 2.82–3.00 (1H, m), 4.01–4.64 (5H, m), 4.70–5.00 (1H, m), 8.05–8.28 (3H, m), 8.72 (1H, dist. t, J=7.9 Hz), 8.84 (1H, br. d, J=5.5 Hz), 9.20 (1H, s), 11.71 (1H, br. s).

EXAMPLE 17

1-Cyclopropyl-6-fluoro-1,4-dihydro-4-oxo-7-[3-(2-pyridinyl)-1-pyrrolidinyl]-3-quinolinecarboxylic acid Starting from 1-cyclopropyl-6,7-difluoro-1,4-dihydro-4-oxo-3-quinolinecarboxylic acid (1.25 g, 4.7 mmol) and 2-(3-pyrrolidinyl)pyridine, a procedure analogous to that given in Example 1 provided the title compound (1.57 g, 85%) as an off-white solid, mp 216°–219° C.

$^1$H-NMR (250 MHz, TFA): $\delta$=1.38–1.46 (2H, m), 1.60–1.69 (2H, m), 2.50–2.70 (1H, m), 2.82–2.98 (1H, m), 3.94–4.32 (5H, m), 4.50–4.67 (1H, m), 7.44 (1H, d, J=7.0 Hz), 8.06–8.23 (3H, m), 8.72 (1H, t, J=7.9 Hz, 8.83 (1H, d, J=5.4 Hz), 9.21 (1H, s), 11.65 (1H, br. s).

EXAMPLE 18

5-Amino-1-cyclopropyl-6,8-difluoro-1,4-dihydro-4-oxo-7-[3-(2-pyridinyl)-1-pyrrolidinyl]-3-quinolinecarboxylic acid Starting from 5-amino-1-cyclopropyl-6,7,8-trifluoro-1,4-dihydro-4-oxo-3-quinolinecarboxylic acid (0.97 g, 2.9 mmol) and 2-(3-pyrrolidinyl)pyridine, a procedure analogous to that given in Example 1 provided the title compound (1.12 g, 91%) as a bright yellow solid, mp 206°–208°C.

$^1$H-NMR (250 MHz, TFA): $\delta$=1.21–1.38 (2H, m), 1.40–1.52 (2H, m), 2.41–2.60 (1H, m), 2.75–2.89 (1H, m), 4.07–4.38 (5H, m), 4.43–4.57 (1H, m), 8.07–8.13 (1H, m), 8.20 (1H, d, J=7.9 Hz), 8.70 (1H, dist. t, J=7.9 Hz), 8.80 (1H, d, J=5.6 Hz), 9.14 (1H, s), 11.65 (1H, br. s).

EXAMPLE 19

1-Cyclopropyl-6-fluoro-1,4-dihydro-4-oxo-7-[3-(2-pyridinyl)-1-pyrrolidinyl]-8-(trifluoromethyl)-3-quinolinecarboxylic acid Starting from 1-cyclopropyl-6,7-difluoro-1,4-dihydro-4-oxo-8-trifluoromethyl-3-quinolinecarboxylic acid (1.33 g, 4.0 mmol) and 2-(3-pyrrolidinyl)pyridine, a procedure analogous to that given Example 1 provided the title compound (1.36 g, 74%) as a yellow solid, mp 210°–212° C.

$^1$H-NMR (250 MHz, TFA): $\delta$=0.98–1.11 (1H, m), 1.13–1.27 (1H, m), 1.43–1.70 (2H, m), 2.45–2.70 (1H, m), 2.81–2.97 (1H, m), 4.12–4.60 (6H, m), 8.05–8.29 (3H, m), 8.63–8.78 (1H, m), 8.86 (1H, dist. d, J=6.0 Hz), 9.40 (1H, s), 11.60 (1H, br. s).

EXAMPLE 20

1-Cyclopropyl-6-fluoro-1,4-dihydro-4-oxo-7-[3-(3-pyridinyl)-1-pyrrolidinyl]-1,8-naphthyridine-3-carboxylic acid Starting from 7-chloro-1-cyclopropyl-6-fluoro-1,4-dihydro-4-oxo-1,8-naphthyridine-3-carboxylic acid (1.24 g, 4.4 mmol) and 3-(3-pyrrolidinyl)pyridine, a procedure analogous to that given in Example 1 provided the title compound (1.43 g, 82%) as a light beige solid, mp 226°–228° C.

$^1$H-NMR (250 MHz, TFA): $\delta$=1.20–1.38 (2H, m), 1.42–1.60 (2H, m), 2.36–2.60 (1H, m), 2.74–2.90 (1H, m), 3.95–4.90 (6H, m), 8.09–8.22 (2H, m), 8.76 (1H, d, J=8.3 Hz), 8.82 (1H, d, J=5.8 Hz), 8.97 (1H, s), 9.17 (1H, s), 11.62 (1H, br. s).

EXAMPLE 21

1-Cyclopropyl-6-fluoro-1,4-dihydro-4-oxo-7-[3-(3-pyridinyl)-1-pyrrolidinyl]-3-quinolinecarboxylic acid Starting from 1-cyclopropyl-6,7-difluoro-1,4-dihydro-4-oxo-3-quinolinecarboxylic acid (1.06 g, 4.0 mmol) and 3-(3-pyrrolidinyl)pyridine, a procedure analogous to that given in Example 1 provided the title compound (1.15 g, 73%) as an off-white solid, mp 233°–236° C.

$^1$H-NMR (250 MHz, TFA): $\delta$=1.35–1.42 (2H, m), 1.59–1.68 (2H, m), 2.39–2.57 (1H, m), 2.72–2.86 (1H, m), 3.92–4.23 (5H, m), 4.47–4.58 (1H, m), 7.42 (1H, d, J=7.1 Hz), 8.15–8.25 (2H, m), 8.78 (1H, d, J=8.4 Hz), 8.84 (1H, d, J=5.8 Hz), 8.98 (1H, br. s), 9.20 (1H, s), 11.63 (1H, br. s).

EXAMPLE 22

5-Amino-1-cyclopropyl-6,8-difluoro-1,4-dihydro-4-oxo-7-[3-(3-pyridinyl)-1-pyrrolidinyl]-3-quinolinecarboxylic acid Starting from 5-amino-1-cyclopropyl-6,7,8-trifluoro-1,4-dihydro-4-oxo-3-quinolinecarboxylic acid (1.04 g, 3.5 mmol) and 3-(3-pyrrolidinyl)pyridine, a procedure analogous to that given in Example 1 provided the title compound (1.26 g, 84%) as a yellow solid, mp 250°–252° C.

$^1$H-NMR (250 MHz, TFA): δ=1.22–1.56 (4H, m), 2.28–2.47 (1H, m), 2.65–2.79 (1H, m), 3.85–4.00 (1H, m), 4.16–4.52 (5H, m), 8.17 (1H, dd, J=8.1, 5.8 Hz), 8.73 (1H, d, J=8.2 Hz), 8.80 (1H, d, J=5.8 Hz), 8.93 (1H, s), 9.12 (1H, s), 11.65 (1H, br. s).

EXAMPLE 23

1-Cyclopropyl-6-fluoro-1,4-dihydro-4-oxo-7-[3-(4-pyridinyl)-1-pyrrolidinyl]-1,8-naphthyridine-3-carboxylic acid Starting from 7-chloro-1-cyclopropyl-6-fluoro-1,4-dihydro-4-oxo-1,8-naphthyridine-3-carboxylic acid (0.85 g, 3.0 mmol) and 4-(3-pyrrolidinyl)pyridine, a procedure analogous to that given in Example 1 provided the title compound (0.79 g, 67%), mp 223°–225° C.

$^1$H-NMR (300 MHz, TFA): δ=1.03–1.12 (2H, m), 1.13–1.24 (2H, m), 2.18–2.28 (1H, m), 2.47–2.60 (1H, m), 3.62–3.76 (1H, m), 3.84–4.00 (3H, m), 4.05–4.18 (1H, m), 4.36–4.44 (1H, m), 8.02 (1H, d, J=12.5 Hz), 8.14 (2H, d, J-5.7 Hz), 8.59 (1H, s), 8.92 (2H, d, J=5.7 Hz), 12.12 (1H, br. s).

EXAMPLE 24

1-Cyclopropyl-6-fluoro-1,4-dihydro-4-oxo-7-[3-(4-pyridinyl)-1-pyrrolidinyl]-3-quinolinecarboxylic acid Starting from 1-cyclopropyl-6,7-difluoro-1,4-dihydro-4-oxo-3-quinolinecarboxylic acid (1.13 g, 4.3 mmol) and 4-(3-pyrrolidinyl)pyridine, a procedure analogous to that given in Example 1 provided the title compound (0.87 g, 52%) as an off-white solid, mp 260°–261° C.

$^1$H-NMR (250 MHz, TFA): δ=1.38–1.47 (2H, m), 1.52–1.72 (2H, m), 2.40–2.60 (1H, m), 2.79–2.94 (1H, m), 3.94–4.20 (5H, m), 4.47–4.63 (1H, m), 7.43 (1H, d, J=7.9 Hz), 8.14–8.21 (3H, m), 8.86 (2H, d, J=5.2 Hz), 9.21(1H, s), 11.65 (1H, br. s).

EXAMPLE 25

5-Amino-1-cyclopropyl-6,8-difluoro-1,4-dihydro-4-oxo-7-[3-(4-pyridinyl)-1-pyrrolidinyl]-3-quinolinecarboxylic acid Starting from 5-amino-1-cyclopropyl-6,7,8-trifluoro-1,4-dihydro-4-oxo-3-quinolinecarboxylic acid (1.10 g, 3.7 mmol) and 4-(3-pyrrolidinyl)pyridine, a procedure analogous to that given in Example 1 provided the title compound (0.75 g, 48%) as a yellow solid, mp 236°–238° C.

$^1$H-NMR (250 MHz, TFA): δ=1.22–1.38 (2H, m), 1.41–1.57 (2H, m), 2.32–2.47 (1H, m), 2.66–2.81 (1H, m), 3.90–4.07 (1H, m), 4.18–4.38 (4H, m), 4.41–4.50 (1H, m), 8.18 (2H, d, J=6.4 Hz), 8.85 (2H, d, J=6.3 Hz), 9.15 (1H, s), 11.62 (1H, br. s).

EXAMPLE 26

1-Cyclopropyl-6-fluoro-1,4-dihydro-4-oxo-7-[3-(4-pyridinyl)-1-pyrrolidinyl]-8-(trifluoromethyl)-3-quinolinecarboxylic acid Starting from 1-cyclopropyl-6,7-difluoro-1,4-dihydro-4-oxo-8-trifluoromethyl-3-quinolinecarboxylic acid (1.05 g, 3.5 mmol) and 4-(3-pyrrolidinyl)pyridine, a procedure analogous to that given in Example 1 provided the title compound (0.93 g, 58%) as a beige solid, mp 244°–245° C.

$^1$H-NMR (250 MHz, TFA): δ=0.99–1.18 (1H, m), 1.19–1.35 (1H, m), 1.43–1.74 (2H, m), 2.37–2.60 (1H, m), 2.75–2.89 (1H, m), 3.98–4.62 (6H, m), 8.08–8.27 (3H, m), 8.81–8.93 (2H, m), 9.39 (1H, s), 11.63 (1H, br. s).

EXAMPLE 27

7-[3-(3-Amino-2-pyridinyl)-1-pyrrolidinyl]-1-cyclopropyl-6-fluoro-1,4-dihydro-4-oxo-3-quinolinecarboxylic acid Starting from 1-cyclopropyl-6,7-difluoro-1,4-dihydro-4-oxo-3-quinolinecarboxylic acid (0.81 g, 3.1 mmol) and 2-(3-pyrrolidinyl)-3-pyridinamine, a procedure analogous to that given in Example 1 provided the title compound (1.15 g, 91%) as an off-white solid, mp>270° C.

$^1$H-NMR (250 MHz, TFA): δ=1.36–1.47 (2H, m), 1.59–1.69 (2H, m), 2.58–2.71 (1H, m), 2.73–2.88 (1H, m), 3.96–4.30 (5H, m), 4.42–4.60 (1H, m), 7.46 (1H, d, J=6.9 Hz), 7.76 (1H, dd, J=8.5, 5.6 Hz), 7.99 (1H, d, J=8.5 Hz), 8.13 (1H, d, J=5.5 Hz), 8.19 (1H, d, J=13.3 Hz), 9.22 (1H, s), 11.63 (1H, br. s).

EXAMPLE 28

7-[3-[3-(Aminomethyl)-2-pyridinyl]-1-pyrrolidinyl]-1-cyclopropyl-6-fluoro-1,4-dihydro-4-oxo-3-quinolinecarboxylic acid Starting from 1-cyclopropyl-6,7-difluoro-1,4-dihydro-4-oxo-3-quinolinecarboxylic acid (0.80 g, 3.0 mmol) and 2-(3-pyrrolidinyl)-3-pyridinemethanamine, a procedure analogous to that given in Example 1 provided the title compound (1.09 g, 86%) as an off-white solid, mp 246°–248° C.

$^1$H-NMR (250 MHz, TFA): δ=1.37–1.45 (2H, m), 1.60–1.68 (2H, m), 2.63–2.80 (1H, m), 2.82–3.00 (1H, m), 3.96–4.14 (2H, m), 4.18–4.29 (1H, m), 4.31–4.40 (1H, m), 4.50–4.70 (2H, m), 5.03 (2H, m), 7.47 (1H, d, J=6.9 Hz), 8.14–8.22 (2H, m), 8.97–9.04 (2H, m), 9.23 (1H, s), 11.65 (1H, br. s).

EXAMPLE 29

5-Amino-7-[3-[3-(aminomethyl)-2-pyridinyl]-1-pyrrolidinyl]-1-cyclopropyl-6,8-difluoro-1,4-dihydro-4-oxo-3-quinolinecarboxylic acid Starting from 5-amino-1-cyclopropyl-6,7,8-trifluoro-1,4-dihydro-4-oxo-3-quinolinecarboxylic acid (0.60 g, 2.0 mmol) and 2-(3-pyrrolidinyl)-3-pyridinemethanamine, a procedure analogous to that given in Example 1 provided the title compound (0.74 g, 81%) as a yellow solid, mp 226°–228° C.

$^1$H-NMR (250 MHz, TFA): δ=1.25–1.38 (2H, m), 1.41–1.57 (2H, m), 2.50–2.72 (1H, m), 2.75–2.90 (1H, m), 4.19–4.39 (3H, m), 4.41–4.60 (3H, m), 5.01 (2H, br. s), 8.17 (1H, dd, J=7.6, 6.3 Hz), 8.93–9.03 (2H, m), 9.15 (1H, s), 11.64 (1H, br. s).

EXAMPLE 30

7-[3-[2-(Aminomethyl)phenyl]-1-pyrrolidinyl]-1-(2,4-difluorophenyl)-6-fluoro-1,4-dihydro-5-methyl-4-oxo-3-quinolinecarboxylic acid Starting from 6,7-difluoro-1-(2,4-difluorophenyl)-1,4-dihydro-5-methyl-4-oxo-3-quinolinecarboxylic acid (0.40 g, 1.1 mmol) and 2-(3-pyrrolidinyl)benzenemethanamine, a procedure analogous to that given in Example 1, provided the title compound (0.40 g, 72%) as a beige solid, mp 283°–285° C. (dec).

$^1$H-NMR (250 MHz, TFA): δ=2.14–2.30 (1H, m), 2.41–2.59 (1H, m), 2.96 (3H, s), 3.65–3.97 (4H, m), 4.04–4.22 (1H, m), 4.47–4.68 (2H, m), 7.21–7.60 (6H, m), 7.62–7.78 (1H, m), 8.98 (1H, s), 11.65 (1, br. s).

EXAMPLE 31

1-(2,4-Difluorophenyl)-6-fluoro-1,4-dihydro-4-oxo-7-[3-(4-pyridinyl)-1-pyrrolidinyl]-1,8-naphthyridine-3-carboxylic acid Starting from 7-chloro-1-(2,4-difluorophenyl)-6-fluoro-1,4-dihydro-4-oxo-1,8-naphthyridine-3-carboxylic acid (0.51 g, 1.5 mmol) and 4-(3-pyrrolidinyl)pyridine, a procedure analogous to that given in Example 1, provided the title compound (0.39 g, 56%) as an off-white solid, mp 253°–255° C. (dec).

$^1$H-NMR (300 MHz, d$_6$-DMSO): δ=1.88–2.10 (1H, m), 2.21–2.40 (1H, m), 3.20–3.60 (5H, m), 7.23–7.39 (3H, m), 7.57–7.68 (1H, m), 7.82 (1H, td, J=8.7, 6.0 Hz), 8.10 (1H, d, J=12.6 Hz), 8.51 (2H, d, J=6.0 Hz), 8.83 (1H, s), 15.18 (1H, br. s).

EXAMPLE 32

3-[1-(3-Carboxy-1-cyclopropyl-6-fluoro-1,4-dihydro-4-oxo-7-quinolyl)-3-pyrrolidinyl]-1-methylpyridinium iodide Iodomethane (1.62 g, 11.4 mmol) was added dropwise to a stirred suspension of 1-cyclopropyl-6-fluoro-1,4-dihydro-4-oxo-7-[3-(3-pyridinyl)-1-pyrrolidinyl]-3-quinolinecarboxylic acid (0.30 g, 0.8 mmol) in acetonitrile (30 mL). The resulting mixture was heated at reflux for 2 hours. The suspension was then filtered, the solids were washed with acetonitrile and ether, and dried in vacuo at 40° C. to give the title compound (0.38 g, 88%) as a light yellow solid, mp 278°–280° C.

$^1$H-NMR (250 MHz, d$_6$-DMSO): δ=1.10–1.20 (2H, m), 1.27–1.38 (2H, m), 2.16–2.39 (1H, m), 2.47–2.60 (1H, m), 1.27–1.38 (2H, m), 2.16–2.39 (1H, m), 2.47–2.60 (1H, m), 3.66–3.95 (5H, m), 4.05–4.18 (1H, m), 4.38 (3H, s), 7.08–7.17 (1H, m), 7.78 (1H, d, J-14.1 Hz), 8.15 (1H, dist. t, J=6.6, 7.3 Hz), 8.55 (1H, s), 8.65 (1H, br. d, J=7.9 Hz), 8.93 (1H, d, J=5.7 Hz), 9.13 (1H, s), 15.42 (1H, br. s).

EXAMPLE 33

4-[1-(3-Carboxy-1-cyclopropyl-6-fluoro-1,4-dihydro-4-oxo-7-quinolyl)-3-pyrrolidinyl]-1-methylpyridinium iodide Starting from 1-cyclopropyl-6-fluoro-1,4-dihydro-4-oxo-7-[3-(4-pyridinyl)-1-pyrrolidinyl]-3-quinolinecarboxylic acid (0.40 g, 1.0 mmol), a procedure analogous to that given in Example 32, provided the title compound (0.50 g, 93%) as a light yellow solid, mp>280° C.

$^1$H-NMR (300 MHz, d$_6$-DMSO): δ=1.12–1.18 (2H, m), 1.23–1.39 (2H, m), 2.17–2.28 (1H, m), 2.50–2.60 (1H, m), 3.70–3.98 (5H, m), 4.10–4.20 (1H, m), 4.32 (3H, s), 7.16 (1H, d, J=7.9 Hz), 7.85 (1H, d, J=14.3 Hz), 8.17 (2H, d, J=6.7 Hz), 8.60 (1H, s), 8.95 (2H, d, J=6.6 Hz), 15.47 (1H, br. s).

We claim:

1. A compound of the formula

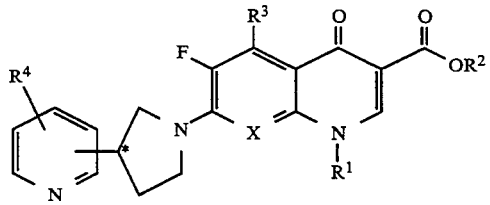

wherein * denotes an asymmetric carbon;

X is C—H, C—F, C—Cl, C—OCH$_3$, C—CF$_3$, or N;

R$^1$ is a C$_1$–C$_4$-alkyl, C$_3$–C$_6$-cycloalkyl, or phenyl substituted by one or more halogen atoms;

R$^2$ is hydrogen, alkyl of 1 to 4 carbon atoms, or a cation;

R$^3$ is hydrogen, amino, or methyl;

R$^4$ is hydrogen or one, two or three substituents independently selected from C$_1$–C$_4$-alkyl, halo-substituted C$_1$–C$_4$-alkyl, hydroxy-substituted C$_1$–C$_4$-alkyl, halogen, hydroxy, C$_1$–C$_4$-alkoxy, mercapto, amino, mono-(C$_1$–C$_4$-alkyl)amino, di-(C$_1$–C$_4$-alkyl)amino, formamido, mono-(C$_1$–C$_4$-alkyl)amide, di-(C$_1$–C$_4$-alkyl)amido, cyano, nitro, C$_1$–C$_4$-alkoxycarbonyl, carboxyl, aminomethyl, mono-(C$_1$–C$_4$-alkyl)aminomethyl, di-(C$_1$–C$_4$-alkyl)aminomethyl, wherein free hydroxy and amino groups may be protected;

or a pharmaceutically acceptable acid addition or quaternary ammonium salt thereof.

2. A compound according to claim 1, wherein R$^1$ is C$_3$–C$_6$-cycloalkyl or phenyl substituted by one or more halogen atoms, and R$^4$ is hydrogen, hydroxy, C$_1$–C$_4$-alkoxy, hydroxy substituted C$_1$–C$_4$-alkyl, amino, mono-(C$_1$–C$_4$-alkyl)amino, di-(C$_1$–C$_4$-alkyl)amino, aminomethyl, mono-(C$_1$–C$_4$-alkyl)aminomethyl, or di-(C$_1$–C$_4$-alkyl)aminomethyl.

3. A compound according to claim 2 wherein X is C—H, C—F, C—Cl, C—OCH$_3$, or N; R$^1$ is cyclopropyl or 2,4-difluorophenyl; R$^3$ is hydrogen or amino, and R$^4$ is hydrogen, hydroxy, hydroxymethyl, amino, methylamino, dimethylamino, aminomethyl, methylaminomethyl, or dimethylaminomethyl.

4. A compound according to claim 3 wherein R$^2$ is hydrogen or a cation, and R$^4$ is hydrogen, hydroxy, hydroxymethyl, amino, or aminomethyl.

5. A compound according to claim 1 and being 1-cyclopropyl-6-fluoro-1,4-dihydro-4-oxo-7-[3-(2-pyridinyl)-1-pyrrolidinyl]-1,8-naphthyridine-3-carboxylic acid.

6. A compound according to claim 1 and being 1-cyclopropyl-6-fluoro-1,4-dihydro-4-oxo-7-[3-(2-pyridinyl)-1-pyrrolidinyl]-3-quinolinecarboxylic acid.

7. A compound according to claim 1 and being 5-amino-1-cyclopropyl-6,8-difluoro-1,4-dihydro-4-oxo-7-[3-(2-pyridinyl)-1-pyrrolidinyl]-3-quinolinecarboxylic acid.

8. A compound according to claim 1 and being 1-cyclopropyl-6-fluoro-1,4-dihydro-4-oxo-7-[3-(3-pyridinyl)-1-pyrrolidinyl]-1,8-naphthyridine-3-carboxylic acid.

9. A compound according to claim 1 and being 1-cyclopropyl-6-fluoro-1,4-dihydro-4-oxo-7-[3-(3-pyridinyl)-1-pyrrolidinyl]-3-quinolinecarboxylic acid.

10. A compound according to claim 1 and being 5-amino-1-cyclopropyl-6,8-difluoro-1,4-dihydro-4-oxo-7-[3-(3-pyridinyl)-1-pyrrolidinyl]-3-quinolinecarboxylic acid.

11. A compound according to claim 1 and being 1-cyclopropyl-6-fluoro-1,4-dihydro-4-oxo-7-[3-(4-pyridinyl)-1-pyrrolidinyl]-1,8-naphthyridine-3-carboxylic acid.

12. A compound according to claim 1 and being 1-cyclopropyl-6-fluoro-1,4-dihydro-4-oxo-7-[3-(4-pyridinyl)-1-pyrrolidinyl]-3-quinolinecarboxylic acid.

13. A compound according to claim 1 and being 5-amino-1-cyclopropyl-6,8-difluoro-1,4-dihydro-4-oxo-7-[3-(4-pyridinyl)-1-pyrrolidinyl]-3-quinolinecarboxylic acid.

14. A compound according to claim 1 and being 7-[3-(3-amino-2-pyridinyl)-1-pyrrolidinyl]-1-cyclopropyl-6-fluoro-1,4-dihydro-4-oxo-3-quinolinecarboxylic acid.

15. A compound according to claim 1 and being 7-[3-[3-(aminomethyl)-2-pyridinyl]-1-pyrrolidinyl]-1-cyclopropyl-6-fluoro-1,4-dihydro-4-oxo-3-quinolinecarboxylic acid.

16. A compound according to claim 1 and being 5-amino-7-[3-[3-(aminomethyl)-2-pyridinyl]-1-pyrrolidinyl]-1-cyclopropyl-6,8-difluoro-1,4-dihydro-4-oxo-3-quinolinecarboxylic acid.

17. A compound according to claim 1 and being 1-(2,4-difluorophenyl)-6-fluoro-1,4-dihydro-4-oxo-7-[3-(3-pyridinyl)-1-pyrrolidinyl]-1,8-naphthyridine-3-carboxylic acid.

18. A pharmaceutical composition comprising an antibacterially effective amount of a compound as claimed in claim 1 together with a pharmaceutically acceptable carrier.

19. A method of treating bacterial infections in mammals which comprises administering to said mammal a pharmaceutical composition as claimed in claim 18 in unit dosage form.

* * * * *